(12) United States Patent
Li et al.

(10) Patent No.: US 7,129,343 B2
(45) Date of Patent: Oct. 31, 2006

(54) BI-DIRECTIONAL DUAL PROMOTER COMPLEX WITH ENHANCED PROMOTER ACTIVITY FOR TRANSGENE EXPRESSION IN EUKARYOTES

(75) Inventors: Zhijian Li, Apopka, FL (US); Dennis Gray, Howy in the Hills, FL (US)

(73) Assignee: University of Florida, Gainesville, FL (US)

( * ) Notice: Subject to any disclaimer, the term of this patent is extended or adjusted under 35 U.S.C. 154(b) by 456 days.

(21) Appl. No.: 10/075,105

(22) Filed: Feb. 13, 2002

(65) Prior Publication Data

US 2005/0188432 A1   Aug. 25, 2005

Related U.S. Application Data

(60) Provisional application No. 60/268,358, filed on Feb. 13, 2001.

(51) Int. Cl.
*C07H 21/04* (2006.01)
*C12N 15/63* (2006.01)
*C12P 21/00* (2006.01)
*C12N 15/85* (2006.01)

(52) U.S. Cl. ............... 536/24.1; 435/320.1; 435/70.1; 435/455

(58) Field of Classification Search ............ None
See application file for complete search history.

(56) References Cited

U.S. PATENT DOCUMENTS

| | | |
|---|---|---|
| 4,966,841 A | 10/1990 | Riley |
| 5,258,294 A | 11/1993 | Boyle et al. |
| 5,368,855 A | 11/1994 | Boyle et al. |
| 5,424,200 A | 6/1995 | McPherson et al. |
| 5,547,862 A | 8/1996 | Meador et al. |
| 5,627,046 A | 5/1997 | Falcone et al. |
| 5,665,578 A | 9/1997 | Gillies |
| 5,691,140 A | 11/1997 | Noren et al. |
| 5,693,508 A | 12/1997 | Chang |
| 5,789,208 A | 8/1998 | Sharon |
| 5,827,693 A | 10/1998 | De Angelo et al. |
| 5,866,755 A | 2/1999 | Bujard et al. |
| 5,876,962 A | 3/1999 | Bishop et al. |
| 5,877,306 A | 3/1999 | Cornelissen et al. |
| 5,891,718 A * | 4/1999 | Hobart et al. ............... 435/325 |
| 5,912,411 A | 6/1999 | Bujard et al. |
| 5,955,646 A | 9/1999 | Gelvin et al. |
| 5,968,773 A | 10/1999 | Heddle et al. |
| 5,990,091 A | 11/1999 | Tartaglia et al. |
| 6,004,777 A | 12/1999 | Tartaglia et al. |
| 6,004,941 A | 12/1999 | Bujard et al. |
| 6,008,051 A | 12/1999 | DasSarma et al. |
| 6,033,670 A | 3/2000 | Bublot et al. |
| 6,043,415 A | 3/2000 | Strizhov et al. |
| 6,117,651 A | 9/2000 | Schultz et al. |
| 6,388,170 B1 | 5/2002 | Gan et al. |

OTHER PUBLICATIONS

Barfield, D., Pua, E.-C. (1991) Gene transfer in plants of *Brassica juncea* using *Agrobacterium tumefaciens*-medicated transformation. Plant Cell Report. 10:308-314.

Pua, E.-C. (1999) Transgenic Brown Mustard (*Brassica juncea*). In Bajaj Y.P.S. (Ed) Transgenic crop I. Biotechnology in Agriculture and Forestry, vol. 46. Springer-Verlag Berlin Heidelberg, pp. 209-224.

Li, Zhijian, "Expression of a Bifunctional Green Fluorescent Protein (GFP) Fusion Marker under the Control of Three Constitutive Promoters and Enhanced Derivatives in Transgenic Grape (Vitis Vinifera)", *Plant Science*, vol. 160, No. 5, Apr. 2001, p. 877-887.

* cited by examiner

*Primary Examiner*—Celine Qian
(74) *Attorney, Agent, or Firm*—Fitch, Even, Tabin & Flannery

(57) ABSTRACT

The present invention is directed to bidirectional promoter complexes that are effective for enhancing transcriptional activity of transgenes. The bidirectional promoters of the invention include a modified enhancer region with at least two core promoters on either side of the modified enhancer in a divergent orientation.

10 Claims, 37 Drawing Sheets

BamHI

1   GGATCCAGCG TGTCCTCTCC AAATGAAATG AACTTCCTTA TATAGAGGAA GGGTCTTGCG AAGGATAGTG GGATTGTGCG
    CCTAGGTCGC ACAGGAGAGG TTTACTTTAC TTGAAGGAAT ATATCTCCTT CCCAGAACGC TTCCTATCAC CCTAACACGC

PstI    HindIII PstI

81  TCATCCCTTA CGTCAGTGGA GATACTGCAG AAGCTTCTGC AGTGAGACTT TTCAACAAAG GGTAATATCG GGAAACCTCC
    AGTAGGGAAT GCAGTCACCT CTATGACGTC TTCGAAGACG TCACTCTGAA AAGTTGTTTC CCATTATAGC CCTTTGGAGG

161 TCGGATTCCA TTGCCCAGCT ATCTGTCACT TCATCAAAAG GACAGTAGAA AAGGAAGGTG GCACCTACAA ATGCCATCAT
    AGCCTAAGGT AACGGGTCGA TAGACAGTGA AGTAGTTTTC CTGTCATCTT TTCCTTCCAC CGTGGATGTT TACGGTAGTA

241 TGCGATAAAG GAAAGGCTAT CGTTCAAGAT GCCTCTGCCG ACAGTGGTCC CAAAGATGGA CCCCCACCCA CGAGGAGCAT
    ACGCTATTTC CTTTCCGATA GCAAGTTCTA CGGAGACGGC TGTCACCAGG GTTTCTACCT GGGGGTGGGT GCTCCTCGTA

321 CGTGGAAAAA GAAGACGTTC CAACCACGTC TTCAAAGCAA GTGGATTGAT GTGATTGCAG TGAGACTTTT CAACAAAGGG
    GCACCTTTTT CTTCTGCAAG GTTGGTGCAG AAGTTTCGTT CACCTAACTA CACTAACGTC ACTCTGAAAA GTTGTTTCCC

401 TAATATCGGG AAACCTCCTC GGATTCCATT GCCCAGCTAT CTGTCACTTC ATCAAAAGGA CAGTAGAAAA GGAAGGTGGC
    ATTATAGCCC TTTGGAGGAG CCTAAGGTAA CGGGTCGATA GACAGTGAAG TAGTTTTCCT GTCATCTTTT CCTTCCACCG

481 ACCTACAAAT GCCATCATTG CGATAAAGGA AAGGCTATCG TTCAAGATGC CTCTGCCGAC AGTGGTCCCA AAGATGGACC
    TGGATGTTTA CGGTAGTAAC GCTATTTCCT TTCCGATAGC AAGTTCTACG GAGACGGCTG TCACCAGGGT TTCTACCTGG

FIG. 2A

```
561  CCCACCCACG AGGAGCATCG TGGAAAAAGA AGACGTTCCA ACCACGTCTT CAAAGCAAGT GGATTGATGT GATATCTCCA
     GGGTGGGTGC TCCTCGTAGC ACCTTTTTCT TCTGCAAGGT TGGTGCAGAA GTTCGTTCA  CCTAACTACA CTATAGAGGT

641  CTGACGTAAG GGATGACGCA CAATCCCACT ATCCTTCGCA AGACCCTTCC TCTATATAAG GAAGTTCATT TCATTTGGAG
     GACTGCATTC CCTACTGCGT GTTAGGGTGA TAGGAAGCGT TCTGGGAAGG AGATATATTC CTTCAAGTAA AGTAAACCTC

BamHI
721  AGGACACGCT GGATCC            Seq. ID No. 1
     TCCTGTGCGA CCTAGG            Seq. ID No. 2
```

FIG. 2B

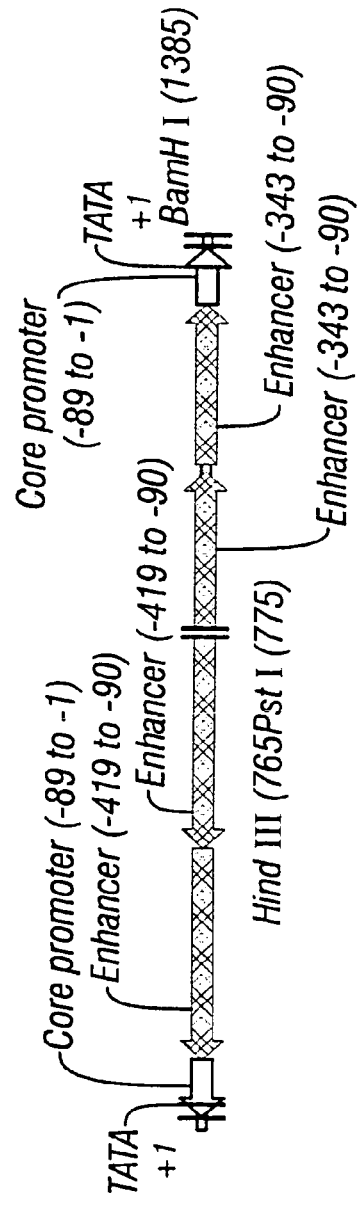

FIG. 3

Seq. ID No. 3
Seq. ID No. 4

```
                SnaBI
                ----
  1  TACGTACAGC GTGTCCTCTC CAAATGAAAT GAACTTCCTT ATATAGAGGA AGGGTCTTGC GAAGGATAGT GGGATTGTGC
     ---------- ---------- ---------- ---------- ---------- ---------- ---------- ----------
     ATGCATGTCG CACAGGAGAG GTTTACTTTA CTTGAAGGAA TATATCTCCT TCCCAGAACG CTTCCTATCA CCCTAACACG

81  GTCATCCCTT ACGTCAGTGG AGATATCACA TCCATCCACT TGCTTTGAAG ACGTGGTTGG AACGTCTTCT TTTCCACGA
     ---------- ---------- ---------- ---------- ---------- ---------- ---------- ----------
     CAGTAGGGAA TGCAGTCACC TCTATAGTGT AGTTAGGTGA ACGAAACTTC TGCACCAACC TTGCAGAAGA AAAGGTGCT

161  TGCTCCTCGT GGGTGGGGGT CCATCTTTGG GACCACTGTC GGCAGAGGCA TCTTCAACGA TGGCCTTTCC TTTATCGCAA
     ---------- ---------- ---------- ---------- ---------- ---------- ---------- ----------
     ACGAGGAGCA CCCACCCCCA GGTAGAAACC CTGGTGACAG CCGTCTCCGT AGAAGTTGCT ACCGGAAAGG AAATAGCGTT

241  TGATGGCATT TGTAGGAGCC ACCTTCCTTT TCCACTATCT TCACAATAAA GTGACAGATA GCTGGGCAAT GGAATCCGAG
     ---------- ---------- ---------- ---------- ---------- ---------- ---------- ----------
     ACTACCGTAA ACATCCTCGG TGGAAGGAAA AGGTGATAGA AGTGTTATTT CACTGTCTAT CGACCCGTTA CCTTAGGCTC

321  GAGGTTTCCG GATATTACCC TTGTTGAAA AGTCTCAATT GCCCTTTGGT CTTCTGAGAC TGTATCTTTG ATATTTTTGG
     ---------- ---------- ---------- ---------- ---------- ---------- ---------- ----------
     CTCCAAAGGC CTATAATGGG AACAACTTT TCAGAGTTAA CGGGAAACCA GAAGACTCTG ACATAGAAAC TATAAAAACC

401  AGTAGACAAG TGTGTCGTGC TCCACCATGT TGATTCACAT ACTAAGTGTA GTTAGGTGAA CGTTTGAAGA CGTGGTTGGA ACGTCTTCTT
     ---------- ---------- ---------- ---------- ---------- ---------- ---------- ----------
     TCATCTGTTC ACACAGCACG AGGTGGTACA ACTAGTGTA CAATTCACAT CGAAACTTCT GCACCAACCT TGCAGAAGAA

481  TTTCCACGAT GCTCCTCGTG GGTGGGGGTC CATCTTTGGG ACCACTGTCG GCAGAGGCAT CTTCAACGAT GGCCTTTCCT
     ---------- ---------- ---------- ---------- ---------- ---------- ---------- ----------
     AAAGGTGCTA CGAGGAGCAC CCACCCCCAG GTAGAAACCC TGGTGACAGC CGTCTCCGTA GAAGTTGCTA CCGGAAAGGA
```

FIG. 4A

```
 561  TTATCGCAAT GATGGCATTT GTAGGAGCCA CCTTCCTTTT CCACTATCTT CACAATAAAG TGACAGATAG CTGGGCAATG
      AATAGCGTTA CTACCGTAAA CATCCTCGGT GGAAGGAAAA GGTGATAGAA GTGTTATTTC ACTGTCTATC GACCCGTTAC

641  GAATCCGAGG AGGTTTCCGG ATATTACCCT TTGTTGAAAA GTCTCAATTG CCCTTTGGTC TTCTGAGACT GTATCTTTGA
      CTTAGGCTCC TCCAAAGGCC TATAATGGGA AACAACTTTT CAGAGTTAAC GGGAAACCAG AAGACTCTGA CATAGAAACT
                                                                   HindIIIPstI
                                                                   ─────────────
 721  TATTTTTGGA GTAGACAAGT GTGTCGTGCT CCACCATGTT GATAAGCTTC TGCAGTGAGA CTTTTCAACA AAGGGTAATA
      ATAAAAACCT CATCTGTTCA CACAGCACGA GGTGGTACAA CTATTCGAAG ACGTCACTCT GAAAAGTTGT TTCCCATTAT 801  TCGGAAACC  TCCTCGGATT CCATTGCCCA GCTATCTGTC ACTTCATCAA AAGGACAGTA GAAAGGAAG  GTGGCACCTA
      AGCCCTTTGG AGGAGCCTAA GGTAACGGGT CGATAGACAG TGAAGTAGTT TCCTGTCAT  CTTTCCTTC  CACCGTGGAT 881  CAAATGCCAT CATTGCGATA AAGGAAAGGC TATCGTTCAA GATGCCTCTG CCGACAGTGG TCCCAAAGAT GGACCCCCAC
      GTTTACGGTA GTAACGCTAT TTCCTTTCCG ATAGCAAGTT CTACGGAGAC GGCTGTCACC AGGGTTTCTA CCTGGGGGTG 961  CCACGAGGAG CATCGTGGAA AAGAAGACG  TTCCAACCAC GTCTTCAAAG CAAGTGGATT GATGTGATTG CAGTGAGACT
      GGTGCTCCTC GTAGCACCTT TTCTTCTGC  AAGGTTGGTG CAGAAGTTTC GTTCACCTAA CTACACTAAC GTCACTCTGA 1041  TTTCAACAAA GGGTAATATC GGGAAACCTC CTCGGATTCC ATTGCCCAGC TATCTGTCAC TTCATCAAAA GGACAGTAGA
      AAAGTTGTTT CCCATTATAG CCCTTTGGAG GAGCCTAAGG TAACGGGTCG ATAGACAGTG AAGTAGTTTT CCTGTCATCT 1121  AAAGGAAGGT GGCACCTACA AATGCCATCA TTGCGATAAA GGAAAGGCTA TCGTTCAAGA TGCCTCTGCC GACAGTGGTC
      TTTCCTTCCA CCGTGGATGT TTACGGTAGT AACGCTATTT CCTTTCCGAT AGCAAGTTCT ACGGAGACGG CTGTCACCAG
```

FIG. 4B

1201 CCAAAGATGG ACCCCCACCC ACGAGGAGCA TCGTTGGAAAA AGAAGAGGTT CCAACCACGT CTTCAAAGCA AGTGGATTGA
     GGTTTCTACC TGGGGGTGGG TGCTCCTCGT AGCACCTTTT TCTTCTGCAA GGTTGGTGCA GAAGTTTCGT TCACCTAACT

1281 TGTGATATCT CCACTGACGT AAGGGATGAC GCACAATCCC ACTATCCTTC GCAAGACCCT TCCTCTATAT AAGGAAGTTC
     ACACTATAGA GGTGACTGCA TTCCCTACTG CGTGTTAGGG TGATAGGAAG CGTTCTGGGA AGGAGATATA TTCCTTCAAG

FIG. 4C

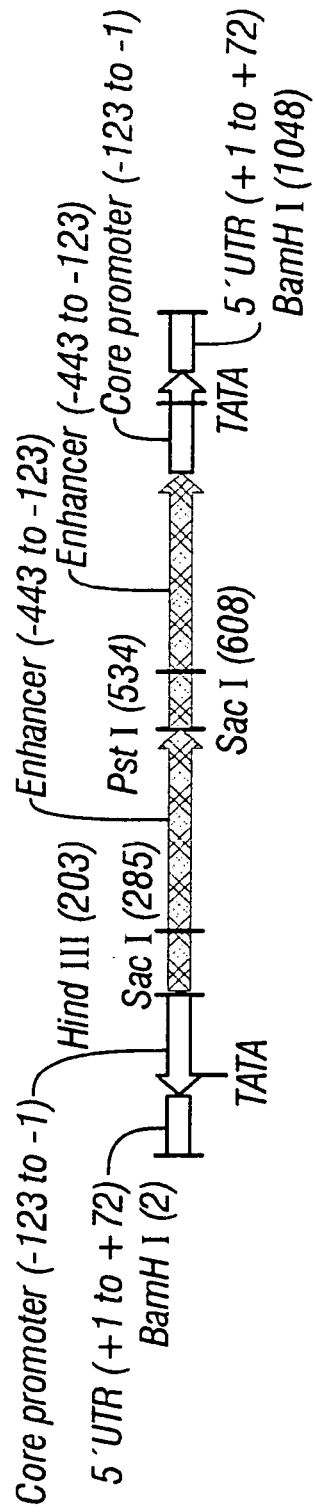

FIG. 5

BamHI
```
  1  GGATCCACAA ACTTACAAAT TTCTCTGAAG TTGTATCCTC AGTACTTCAA AGAAAATAGC TTACACCAAA TTTTTTCTTG
     CCTAGGTGTT TGAATGTTTA AAGAGACTTC AACATAGGAG TCATGAAGTT TCTTTTATCG AATGTGGTTT AAAAAAGAAC

81  TTTTCACAAA TGCCGAACTT GGTTCCTTAT ATAGGAAAAC TCAAGGGCAA AAATGACACG GAAAAATATA AAAGGATAAG
     AAAAGTGTTT ACGGCTTGAA CCAAGGAATA TATCCTTTTG AGTTCCCGTT TTTACTGTGC CTTTTTATAT TTTCCTATTC
```
                                                              HindIII
```
161  TAGTGGGGGA TAAGATTCCT TTGTGATAAG GTTACTTTCC GAAGCTTCCA GAAGGTAATT ATCCAAGATG TAGCATCAAG
     ATCACCCCCT ATTCTAAGGA AACACTATTC CAATGAAAGG CTTCGAAGGT CTTCCATTAA TAGGTTCTAC ATCGTAGTTC
```
                                                SacI
```
241  AATCCAATGT TTACGGGAAA AACTATGGAA GTATTATGTG AGCTCAGCAA GAAGCAGATC AATATGCGGC ACATATGCAA
     TTAGGTTACA AATGCCCTTT TTGATACCTT CATAATACAC TCGAGTCGTT CTTCGTCTAG TTATACGCCG TGTATACGTT 321  CCTATGTTCA AAAATGAAGA ATGTACAGAT ACAAGATCCT ATACTGCCAG AATACGAAGA AGAATACGTA GAAATTGAAA
     GGATACAAGT TTTTACTTCT TACATGTCTA TGTTCTAGGA TATGACGGTC TTATGCTTCT TCTTATGCAT CTTTAACTTT 401  AAGAGAACC AGGCGAAGAA AAGAATCTTG AAGACGTAAG TTCTGCATTC AGAGAAGAAT CACTGACGAC AACAATGAAA AAGGTCGGTG
     TTCTCTTGG TCCGCTTCTT TTCTTAGAAC TTCTGCATTC GTGACTGCTG TTGTTACTTT TCTTCTTCTA TTCCAGCCAC
```

FIG. 6A

```
                                                                                        PstI
                                                                                        ---
481   ATTGTGAAAG AGACATAGAG GACACATGTA AGGTGGAAAA TGTAAGGGCT GCAGAAGGTA ATTATCCAAG ATGTAGCATC
      TAACACTTTC TCTGTATCTC CTGTGTACAT TCCACCTTTT ACATTCCCGA CGTCTTCCAT TAATAGGTTC TACATCGTAG

SacI
                                            ----
561   AAGAATCCAA TGTTTACGGG AAAAACTATG GAAGTATTAT GTGAGCTCAG CAAGAAGCAG ATCAATATGC GGCACATATG
      TTCTTAGGTT ACAAATGCCC TTTTTGATAC CTTCATAATA CACTCGAGTC GTTCTTCGTC TAGTTATACG CCGTGTATAC

641   CAACCTATGT TCAAAAATGA AGAATGTACA GATACAAGAT CCTATACTGC CAGAATACGA AGAAGAATAC GTAGAAATTG
      GTTGGATACA AGTTTTTACT TCTTACATGT CTATGTTCTA GGATATGACG GTCTTATGCT TCTTCTTATG CATCTTTAAC

721   AAAAGAAGA  ACCAGGCGAA GAAAGAATC  TTGAAGACGT AAGCACTGAC GACAACAATG AAAAGAAGAA GATAAGGTCG
      TTTTCTTCT  TGGTCCGCTT CTTTCTTAG  AACTTCTGCA TTCGTGACTG CTGTTGTTAC TTTTCTTCTT CTATTCCAGC

801   GTGATTGTGA AAGAGACATA GAGGACACAT GTAAGGTGGA AAATGTAAGG GCGGAAAGTA ACCTTATCAC AAAGGAATCT
      CACTAACACT TTCTCTGTAT CTCCTGTGTA CATTCCACCT TTTACATTCC CGCCTTTCAT TGGAATAGTG TTTCCTTAGA

881   TATCCCCCAC TACTTATCCT TTTATATTTT TCCGTGTCAT TTTTGCCCTT GAGTTTTCCT ATATAAGGAA CCAAGTTCGG
      ATAGGGGGTG ATGAATAGGA AAATATAAAA AGGCACAGTA AAAACGGGAA CTCAAAAGGA TATATTCCTT GGTTCAAGCC

961   CATTTGTGAA AACAAGAAAA AATTGGTGT  AAGCTATTTT CTTGAAGTA  CTGAGGATAC AACTTCAGAG AAATTGTAA
      GTAAACACTT TTGTTCTTTT TTAACCACA  TTCGATAAAA GAACTTCAT  GACTCCTATG TTGAAGTCTC TTTAAACATT
```

FIG. 6B

```
        BamHI
        ────
1041  GTTTGTGGAT CC      Seq. ID No. 5
      CAAACACCTA GG      Seq. ID No. 6
```

BamHI
1   GGATCCACAA ACTTACAAAT TTCTCTGAAG TTGTATCCTC AGTACTTCAA AGAAAATAGC TTACACCAAA TTTTTTCTTG
    CCTAGGTGTT TGAATGTTTA AAGAGACTTC AACATAGGAG TCATGAAGTT TCTTTTATCG AATGTGGTTT AAAAAAGAAC

81  TTTTCACAAA TGCCGAACTT GGTTCCTTAT ATAGGAAAAC TCAAGGGCAA AAATGACACG GAAAAATATA AAAGGATAAG
    AAAGTGTTT ACGGCTTGAA CCAAGGAATA TATCCTTTTG AGTTCCCGTT TTTACTGTGC CTTTTTATAT TTTCCTATTC

161 TAGTGGGGGA TAAGATTCCT TTGTGATAAG GTTACTTTCC GCCCTTACAT TTTCCACCTT ACATGTGTCC TCTATGTCTC
    ATCACCCCCT ATTCTAAGGA AACACTATTC CAATGAAAGG CGGGAATGTA AAAGGTGGAA TGTACACAGG AGATACAGAG

241 TTTCACAATC ACCGACCTTA TCTTCTTCTT TCATTGTGTG TCGTCAGTGC TTACGTCTTC AAGATTCTTT TCTTCGCCTG
                                                                SacI
    AAAGTGTTAG TGGCTGGAAT AGAAGAAGAA AGTAACAAC AGCAGTCACG AATGCAGAAG TTCTAAGAAA AGAAGCGGAC

321 GTTCTTCTT TTCAATTTCT ACGTATTCTT CTTGTATTC TGGCAGTATA GGATCTGTA TCTGTACATT AGACATGTAA
                                                                                PstI
    CAAGAAGAAA AAGTTAAAGA TGCATAAGAA GAACATAAG ACCGTCATAT CCTAGACAT AGACATGTAA GAAGTAAAAA

401 GAACATAGGT TGCATATGTG CCGCATATTG ATCTGCTTCT TGCTGAGCTC ACATAATACT TCCATAGCTG CAGCCCTTAC
    CTTGTATCCA ACGTATACAC GGGCTATAAC TAGACGAAGA ACGACTCGAG TGTATTATGA AGGTATCGAC GTCGGGAATG

481 ATTTTCCACC TTACATGTGT CCTCTATGTC TCTTTCACAA TCACCGACCT TATCTTCTTC TTTCATTGT TGTCGTCAGT
    TAAAAGGTGG AATGTACACA GGAGATACAG AGAAAGTGTT AGTGGCTGGA ATAGAGAAG AAAGTAACA ACAGCAGTCA

FIG. 8A

```
561  GCTTACGTCT TCAAGATTCT TTTCTTCGCC TGGTTCTTCT TTTTCAATTT CTACGTATTC TTCTTCGTAT TCTGGCAGTA
     CGAATGCAGA AGTTCTAAGA AAAGAAGCGG ACCAAGAAGA AAAAGTTAAA GATGCATAAG AAGAAGCATA AGACCGTCAT
                                                                                                    SacI
                                                                                                   ────

641  TAGGATCTTG TATCTGTACA TTCTTCATTT TTGAACATAG GTTGCATATG TGCCGCATAT TGATCTGCTT CTTGCTGAGC
     ATCCTAGAAC ATAGACATGT AAGAAGTAAA AACTTGTATC CAACGTATAC ACGGCGTATA ACTAGACGAA GAACGACTCG
          SacI                   HindIII
         ────                    ───────

721  TCACATAATA CTTCCATAGG AAGCTTCAGA AGGTAATTAT CCAAGATGTA GCATCAAGAA TCCAATGTTT ACGGGAAAAA
     AGTGTATTAT GAAGGTATCC TTCGAAGTCT TCCATTAATA GGTTCTACAT CGTAGTTCTT AGGTTACAAA TGCCCTTTTT
              SacI
             ────

801  CTATGGAAGT ATTATGTGAG CTCAGCAAGA AGCAGATCAA TATGCGGCAC ATATGCAACC TATGTTCAAA AATGAAGAAT
     GATACCTTCA TAATACACTC GAGTCGTTCT TCGTCTAGTT ATACGCCGTG TATACGTTGG ATACAAGTTT TTACTTCTTA

881  GTACAGATAC AAGATCCTAT ACTGCCAGAA TACGAAGAAG AATACGTAGA AATTGAAAAA GAAGAACCAG GCGAAGAAAA
     CATGTCTATG TTCTAGGATA TGACGGTCTT ATGCTTCTTC TTATGCATCT TTAACTTTTT CTTCTTGGTC CGCTTCTTTT

961  GAATCTTGAA GACGTAAGCA CTGACGACAA CAATGAAAAG AAGAAGATAA GGTCGGTGAT TGTGAAAGAG ACATAGAGGA
     CTTAGAACTT CTGCATTCGT GACTGCTGTT GTTACTTTTC TTCTTCTATT CCAGCCACTA ACACTTTCTC TGTATCTCCT
                 PstI
                ────
```

FIG. 8B

```
1041  CACATGTAAG GTGGAAAATG TAAGGGCTGC AGAAGGTAAT TATCCAAGAT GTAGCATCAA GAATCCAATG TTTACGGGAA
      GTGTACATTC CACCTTTTAC ATTCCCGACG TCTTCCATTA ATAGGTTCTA CATCGTAGTT CTTAGGTTAC AAATGCCCTT
                                                    SacI

1121  AAACTATGGA AGTATTATGT GAGCTCAGCA AGAAGCAGAT CAATATGCGG CACATATGCA ACCTATGTTC AAAAATGAAG
      TTTGATACCT TCATAATACA CTCGAGTCGT TCTTCGTCTA GTTATACGCC GTGTATACGT TGGATACAAG TTTTTACTTC

1201  AATGTACAGA TACAAGATCC TATACTGCCA GAATACGAAG AAGAATACGT AGAAATTGAA AAAGAAGAAC CAGGGGAAGA
      TTACATGTCT ATGTTCTAGG ATATGACGGT CTTATGCTTC TTCTTATGCA TCTTTAACTT TTTCTTCTTG GTCCGCTTCT

1281  AAAGAATCTT GAAGACGTAA GCACTGACGA CAACAATGAA AAGAAGAAGA TAAGGTCGGT GATTGTGAAA GAGACATAGA
      TTTCTTAGAA CTTCTGCATT CGTGACTGCT GTTGTTACTT TTCTTCTTCT ATTCCAGCCA CTAACACTTT CTCTGTATCT

1361  GGACACATGT AAGGTGGAAA ATGTAAGGGC GGAAAGTAAC CTTATCACAA AGGAATCTTA TCCCCACTA CTTATCCTTT
      CCTGTGTACA TTCCACCTTT TACATTCCCG CCTTTCATTG GAATAGTGTT TCCTTAGAAT AGGGGGTGAT GAATAGGAAA

1441  TATATTTTC CGTGTCATTT TTGCCCTTGA GTTTTCCTAT ATAAGGAACC AAGTTCGGCA TTTGTGAAAA CAAGAAAAAA
      ATATAAAAAG GCACAGTAAA AACGGGAACT CAAAAGGATA TATTCCTTGG TTCAAGCCGT AAACACTTTT GTTCTTTTTT
                                                                  BamHI

1521  TTTGGTGTAA GCTATTTTCT TTGAAGTACT GAGGATACAA CTTCAGAGAA ATTTGTAAGT TTGTGGATCC    Seq. ID No. 7
      AAACCACATT CGATAAAAGA AACTTCATGA CTCCTATGTT GAAGTCTCTT TAAACATTCA AACACCTAGG    Seq. ID No. 8
```

FIG. 8C

```
        BamHI
        ‾‾‾‾
  1  GGATCCTTGT TTTCAAAGCG GAGAGGAAAA TATATGAATT TATATAGGCG GGTTTATCTC TTACAACTTT ATTTTCGGCC
     CCTAGGAACA AAAGTTTCGC CTCTCCTTTT ATATACTTAA ATATATCCGC CCAAATAGAG AATGTTGAAA TAAAAGCCGG

HindIII
                                                                 ‾‾‾‾‾‾‾
 81  TTTCAAAAAA ATAATTAAAA TCGACAGACA CGAATCATTT CGACCACAGA AGCTTCAACT ATTTTTATGT ATGCAAGAGT
     AAAGTTTTTT TATTAATTTT AGCTGTCTGT GCTTAGTAAA GCTGGTGTCT TCGAAGTTGA TAAAAATACA TACGTTCTCA 161  CAGCATATGT ATAATTGATT CAGAATCGTT TTGACGAGTT CGGATGTAGT AGTAGCCATT ATTTAATGTA CATACTAATC
     GTCGTATACA TATTAACTAA GTCTTAGCAA AACTGCTCAA GCCTACACTA TCATCGGTAA TAAATTACAT GTATGATTAG 241  GTGAATAGTG ATATGATGAA ACATTGTATC TTATTGTATA AATATCCATA AACACATCAT GAAAGACACT TCTTTCACG
     CACTTATCAC TATACTACTT TGTAACATAG AATAACATAT TTATAGGTAT TTGTGTAGTA CTTTCTGTGA AGAAAGTGC 321  GTCTGAATTA ATTATGATAC AATTCTAATA GAAAACGAAT TAAATTACGT TGAATTGTAT GAAATCTAAT TGAACAAGCC
     CAGACTTAAT TAATACTATG TTAAGATTAT CTTTTGCTTA ATTTAATGCA ACTTAACATA CTTTAGATTA ACTTGTTCGG 401  AACCACGACG ACGACTAACG TTGCCTGGAT TGACTCGGTT TAAGTTAACC ACTAAAAAAA CGGAGCTGTC ATGTAACACG
     TTGGTGCTGC TGCTGATTGC AACGGACCTA ACTGAGCCAA ATTCAATTGG TGATTTTTTT GCCTCGACAG TACATTGTGC 481  CGGATCGAGC AGGTCACAGT CATGAAGCCA TCAAAGCAAA AGAACTAATC CAAGGGCTGA GATGATTAAT TAGTTTAAAA
     GCCTAGCTCG TCCAGTGTCA GTACTTCGGT AGTTTCGTTT TCTTGATTAG GTTCCCGACT CTACTAATTA ATCAAATTTT PstI
                                                            ‾‾‾‾
```

*FIG. 10A*

```
 561  ATTAGTTAAC ACGAGGGAAA AGGCTGTCTG ACAGCCAGGT CACGTTATCT TTACCTGCAG CAACTATTTT TATGTATGCA
      TAATCAATTG TGCTCCCTTT TCCGACAGAC TGTCGGTCCA GTGCAATAGA AATGGACGTC GTTGATAAAA ATACATACGT

641  AGAGTCAGCA TATGTATAAT TGATTCAGAA TCGTTTTGAC GAGTTCGGAT GTAGTAGTAG CCATTATTTA ATGTACATAC
      TCTCAGTCGT ATACATATTA ACTAAGTCTT AGCAAAACTG CTCAAGCCTA CATCATCATC GGTAATAAAT TACATGTATG

721  TAATCGTGAA TAGTGATATG ATGAAACATT GTATCTTATT CCATAAACAC ATCATGAAAG ACACTTTCTT
      ATTAGCACTT ATCACTATAC TACTTTGTAA CATAGAATAA CATATTTATA GGTATTTGTG TAGTACTTTC TGTGAAAGAA

801  TCACGGTCTG AATTAATTAT GATACAATTC TAATAGAAAA CGAATTAAAT TACGTTGAAT TGTATGAAAT CTAATTGAAC
      AGTGCCAGAC TTAATTAATA CTATGTTAAG ATTATCTTTT GCTTAATTTA ATGCAACTTA ACATACTTTA GATTAACTTG

881  AAGCCAACCA CGACGACGAC TAACGTTGCC TGGATTGACT CGGTTTAAGT TAACCACTAA AAAAACGGAG CTGTCATGTA
      TTCGGTTGGT GCTGCTGCTG ATTGCAACGG ACCTAACTGA GCCAAATTCA ATTGGTGATT TTTTTGCCTC GACAGTACAT

961  ACACGCGGAT CGAGCAGGTC ACAGCATCGA AGCCATCAAA GCAAAAGAAC TAATCCAAGG GCTGAGATGA TTAATTAGTT
      TGTGCGCCTA GCTCGTCCAG TGTCAGTAGCT TCGGTAGTTT CGTTTTCTTG ATTAGGTTCC CGACTCTACT AATTAATCAA

1041  ACACGCGGAT CGAGCAGGTC ACAGCATCGA AGCCATCAAA GCAAAAGAAC TAATCCAAGG GCTGAGATGA TTAATTAGTT
      ATTTTTAATC AATTGTGCTC CCTTTTCCGA CAGACTGTCG GTCCAGTGCA ATAGAAATGG ACACCAGCTT TACTAAGCAC

1121  TCTGTCGATT TTAATTATTT TTTTGAAAGG CCGAAAATAA AGTTGTAAGA GATAAACCCG CCTATATAAA TTCATATATT
      AGACAGCTAA AATTAATAAA AAAACTTTCC GGCTTTTATT TCAACATTCT CTATTTGGGC GGATATATATT AAGTATATAA
```

BamHI

*FIG. 10B*

1201 TTCCTCTCCG CTTTGAAAAC AAGGATCC        Seq. ID No. 9
     AAGGAGAGGC GAAACTTTTG TTCCTAGG         Seq. ID No. 10

FIG. 10C

BamHI

1   GGATCCTTTT GGGTTTTGGT GAGAAACAAG GAATAGTATG GATGGGTTTT AATAGGGAAT AAGAGTTGAA AAGTCTGCAA
    CCTAGGAAAA CCCAAAACCA CTCTTTGTTC CTTATCATAC CTACCCAAAA TTATCCCTTA TTCTCAACTT TTCAGACGTT

HindIII

81  TTTGTAAAAG AAAAAAATTG GAAAGTCACA TGTTAGCAGA AGCTTCAGAC TCATTAACTT AAAAGAAGAT ATAGACTCAT
    AAACATTTTC TTTTTTTAAC CTTTCAGTGT ACAATCGTCT TCGAAGTCTG AGTAATTGAA TTTTCTTCTA TATCTGAGTA

161 TAACTTAAAA GAAGATATAG ATTCCAACAC AAGTTCAAAA TTCATAAACG TCAATCTTGG CTAAATTTCT GAACATCAAT
    ATTGAATTTT CTTCTATATC TAAGGTTGTG TTCAAGTTTT AAGTATTTGC AGTTAGAACC GATTTAAAGA CTTGTAGTTA

241 GCATTCCTTT AAAATATAGA TAATAAGTTA GGATGTTGTC ACTTTCTTAA AGCATATTCC GACTGAGTCT GGTAGAATCT
    CGTAAGGAAA TTTTATATCT ATTATTCAAT CCTACACAAG TGAAAGAATT TCGTATAAGG CTGACTCAGA CCATCTTAGA

321 CATAAACTTT AGGCCTTATC TCTTCAATTA GGCAATTACT TACCTCCGCT CTACTTTAAG AAAATTCAAT GGAGTACACC
    GTATTTGAAA TCCGGAATAG AGAAGTTAAT CCGTTAATGA ATGGAGGCGA GATGAAATTC TTTTAAGTTA CCTCATGTGG

FIG. 12A

```
401  ATTATTAAGT TCATATAAAA ATAAAATTAT ATTAATTCTG TCTCTTGTTG GTTCGCTCTA TCTTTTTCTG TTTTCCTGCT
     TAATAATTCA AGTATATTTT TATTTAATA TAATTAAGAC AGAGAACAAC CAAGCGAGAT AGAAAAAGAC AAAAGGACGA

481  TCAACCATAA CATATACAAG AACTACATTT TCCAAGCTAG ATATATCTAA CATGACTGAC TTTGTAAATT TCTTTTGCCA
     AGTTGGTATT GTATATGTTC TTGATGTAAA AGGTTCGATC TATATAGATT GTACTGACTG AAACATTTAA AGAAAACGGT

561  AGTTAAAGAA AAAAAATGAT GTTATCCAAA TAATAAAGAG AAAGAGCCCT AATGAAAAAA ATGATTTACT ATTAGAGTTG
     TCAATTTCTT TTTTTTACTA CAATAGGTTT ATATTTCTC TTTCTCGGGA TTACTTTTT TACTAAATGA TAATCTCAAC

641  TTCAGCTAAT CACATCAATT ATGGTTTTCA TCAAGTATGA CTAATGGCGG CTCTTATCTC AGCTGATGTG ACATTGAAAT
     AAGTCGATTA GTGTAGTTAA TACCAAAAGT AGTTCATACT GATTACCGCC GAGAATAGAG TGCACTACAC TGTAACTTTA
                                                                 PstI
                                                                 ─────

721  TCTTTGACTT TAACACTAAT GTCATATGCT TTCAAATTAA TAATCGATA AAGCTGCAGA CTCATTAACT TAAAGAAGA
     AGAAACTGAA ATTGTGATTA CAGTATACGA AAGTTTAATT ATTAGGCTAT TTCGACGTCT GAGTAATTGA ATTTTCTTCT

801  TATAGACTCA TTAACTTAAA AGAAGATATA GATTCCAACA CAAGTTCAAA ATTCATAAAC GTCAATCTTG GCTAAATTTC
     ATATCTGAGT AATTGAATTT TCTTCTATAT CTAAGGTTGT GTTCAAGTTT TAAGTATTTG CAGTTAGAAC CGATTTAAAG

881  TGAACATCAA TGCATTCCTT TAAAATATAG ATAATAAGTT AGGATGTTGT CACTTCTTA AAGCATATTC CGACTGAGTC
     ACTTGTAGTT ACGTAAGGAA ATTTTATATC TATTATTCAA TCCTACAACA GTGAAAGAAT TTCGTATAAG GCTGACTCAG

961  TGGTAGAATC TCATAAACTT TAGGCCTTAT CTCTTCAATT AGGCAATTAC TTACCTCCGC TCTACTTTAA GAAAATTCAA
     ACCATCTTAG AGTATTTGAA ATCCGGAATA GAGAAGTTAA TCCGTTAATG AATGGAGGCG AGATGAAAT CTTTTAAGTT
```

*FIG. 12B*

1041  TGGAGTACAC CATTATTAAG TTCATATAAA AATAAAATTA TATTAATTCT GTCTCTTGTT GGTTCGCTCT ATCTTTTTCT
      ACCTCATGTG GTAATAATTC AAGTATATTT TTATTTTAAT ATAATTAAGA CAGAGAACAA CCAAGCGAGA TAGAAAAAGA

1121  GTTTTCCTGC TTCAACCATA ACATATACAA GAACTACATT TTCCAAGCTA GATATATCTA ACATGACTGA CTTTGTAAAT
      CAAAAGGACG AAGTTGGTAT TGTATATGTT CTTGATGTAA AAGGTTCGAT CTATATAGAT TGTACTGACT GAAACATTTA

1201  TTCTTTTGCC AAGTTAAAGA AAAAAAATGA TGTTATCCAA ATAATAAAGA GAAAGAGCCC TAATGAAAAA AATGATTTAC
      AAGAAAACGG TTCAATTTCT TTTTTTTACT ACAATAGGTT TATTATTTCT CTTTCTCGGG ATTACTTTT TTACTAAATG

1281  TATTAGAGTT GTTCAGCTAA TCACATCAAT TATGGTTTTC ATCAAGTATG ACTAATGGCG GCTCTTATCT CACGTGATGT
      ATAATCTCAA CAAGTCGATT AGTGTAGTTA ATACCAAAAG TAGTTCATAC TGATTACCGC CGAGAATAGA GTGCACTACA

1361  GACATTGAAA TTCTTTGACT TTAACACTAA TGTCATATGC TTTCAAATTA ATAATCCGAT AAAGTCTGCT AACATGTGAC
      CTGTAACTTT AAGAAACTGA AATTGTGATT ACAGTATACG AAAGTTTAAT TATTAGGCTA TTTCAGACGA TTGTACACTG

1441  TTTCCAATTT TTTTCTTTTA CAAATTGCAG ACTTTTCAAC TCTTATTCCC TATTAAAACC CATCCATACT ATTCCTTGTT
      AAAGGTTAAA AAAAGAAAAT GTTTAACGTC TGAAAAGTTG AGAATAAGGG ATAATTTTGG GTAGGTATGA TAAGGAACAA

1521  TCTCACCAAA ACCCAAAAGG ATCC
      AGAGTGGTTT TGGGTTTTCC TAGG
                        ‾‾‾‾
                        BamHI

Seq. ID No. 11
Seq. ID No. 12

FIG. 12C

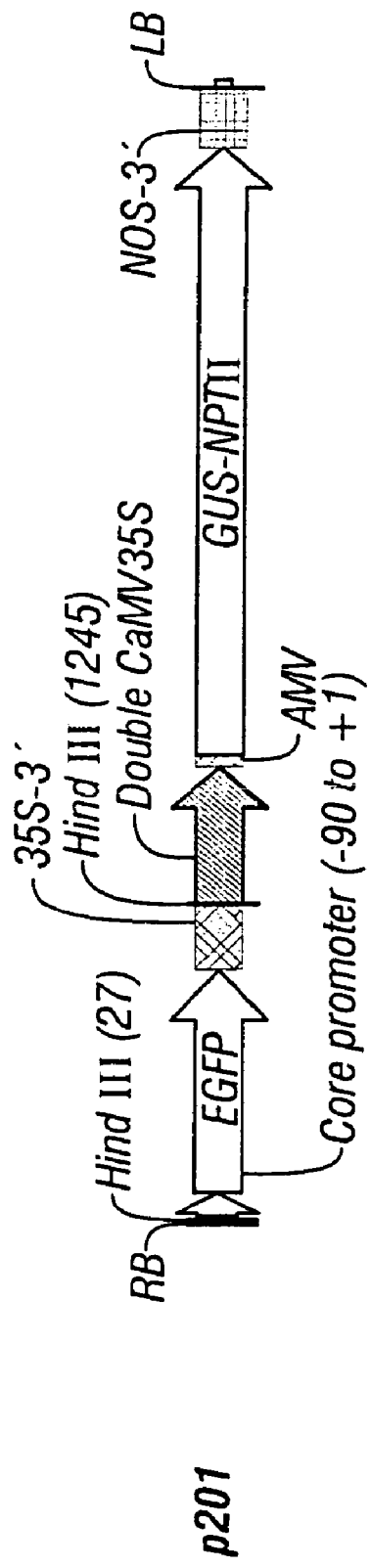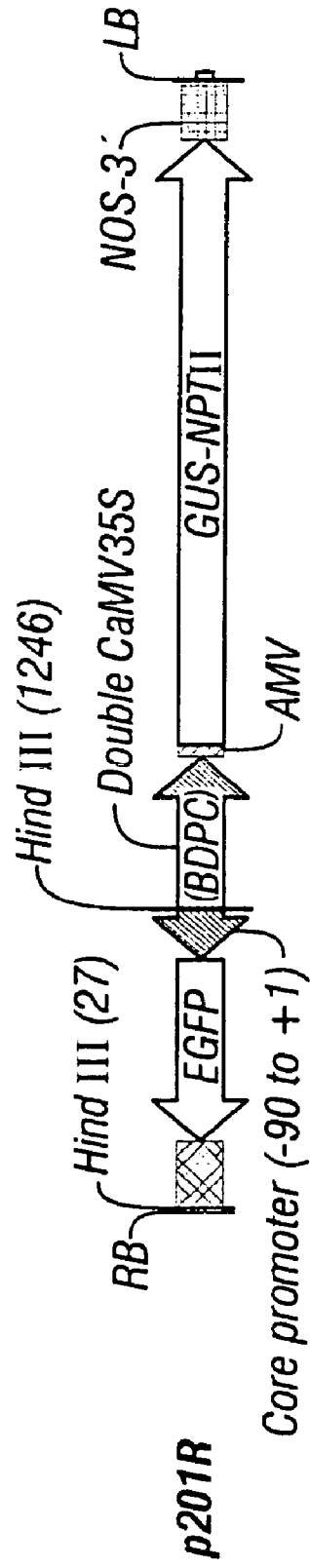
FIG. 13A
FIG. 13B

BamHI

1   GGATCCCTTT TGTGTTTCGT CTTCTCTCAC GTAGAAACCC TAAACAAGGA GGAGGCGGGT TTATATATGT CAATGTACGC
    CCTAGGGAAA ACACAAAGCA GAAGAGAGTG CATCTTTGGG ATTGTTCCT CCTCCGCCCA AATATATACA GTTACATGCG

HindIII

81  GTCTAGGGTT TTGCTAATAT TGGGCTAGGT TACAGGCCTT TACCACAAAA GCTTAGTTGA TAAAATATTT TTATTTGGTT
    CAGATCCCAA AACGATTATA ACCCGATCCA ATGTCCGGAA ATGGTGTTTT CGAATCAACT ATTTTATAAA AATAAACCAA

161 GTAATTTTGT AATATCCCGG GATATTTCAC AAATTGAACA TAGACTACAG AATTTTAGAA AACAAACTTT CTCTCTCTTA
    CATTAAAACA TTATAGGGCC CTATAAAGTG TTTAACTTGT ATCTGATGTC TTAAAATCTT TTGTTTGAAA GAGAGAGAAT

241 TCTCACCTTT ATCTTTTAGA GAGAAAAAGT TCGATTTCCG GTTGACCGGA ATGTATCTTT GTTTTTTTTG TTTTGTAACA
    AGAGTGGAAA TAGAAAATCT CTCTTTTTCA AGCTAAAGGC CAACTGGCCT TACATAGAAA CAAAAAAAAC AAAACATTGT

321 TATTTCGTTT TCCGATTTAG ATCGGATCTC CTTTTCCGTT TGGTCGGACC TTCTTCCGGT TTATCCGGAT CTAATAATAT
    ATAAAGCAAA AGGCTAAATC TAGCCTAGAG GAAAAGGCAA AACAGCCTGG AAGAAGGCCA AATAGGCCTA GATTATTATA

401 CCATCTTAGA CTTAGCTAAG TTTGGATCTG TTTTTGGTT AGCTCTTGTC AATCGCCTCA TCATCAGCAA GAAGGTGAAA
    GGTAGAATCT GAATCGATTC AAACCTAGAC AAAAAACCAA TCGAGAACAG TTAGCGGAGT AGTAGTCGTT CTTCCACTTT

481 TTTTTGACAA ATAAATCTTA GAATCATGTA GTGTCTTTGG ACCTTGGGAA TGATAGAAAC GATTTGTTAT AGCTACTCTA
    AAAAACTGTT TATTTAGAAT CTTAGTACAT CACAGAAACC TGGAACCCTT ACTATCTTTG CTAAACAATA TCGATGAGAT

FIG. 19A

```
561   TGTATCAGAC CCTGACCAAG ATCCAACAAT CTCATAGGTT TTGTGCATAT GAAACCTTCG ACTAACGAGA AGTGGTCTTT
      ACATAGTCTG GGACTGGTTC TAGGTTGTTA GAGTATCCAA AACACGTATA CTTTGGAAGC TGATTGCTCT TCACCAGAAA

641   TAATGAGAGA GATATCTAAA ATGTTATCTT AAAAGCCCAC TCAAATCTCA AGGCATAAGG TAGAAATGCA AATTTGGAAA
      ATTACTCTCT CTATAGATTT TACAATAGAA TTTTCGGGTG AGTTTAGAGT TCCGTATTCC ATCTTTACGT TTAAACCTTT
                                                PstI

721   GTGGGCTGGG CCTTCTGCAG TTGATAAAAT ATTTTTATTT GGTTGTAATT TTGTAATATC CCGGGATATT TCACAAATTG
      CACCCGACCC GGAAGACGTC AACTATTTTA TAAAAATAAA CCAACATTAA AACATTATAG GGCCCTATAA AGTGTTTAAC

801   AACATAGACT ACAGAATTTT AGAAAACAAA CTTTCTCTCT CTTATCTCAC CTTTATCTTT TAGAGAGAAA AAGTTCGATT
      TTGTATCTGA TGTCTTAAAA TCTTTTGTTT GAAAGAGAGA GAATAGAGTG GAAATAGAAA ATCTCTCTTT TTCAAGCTAA

881   TCCGGTTGAC CGGAATGTAT CTTTGTTTTT TTTGTTTTGT AACATATTTC GTTTTCCGAT TTAGATCGGA TCTCCTTTTC
      AGGCCAACTG GCCTTACATA GAAACAAAAA AAACAAAACA TTGTATAAAG CAAAAGGCTA AATCTAGCCT AGAGGAAAAG

961   CGTTTTGTCG GACCCTCTTC CGGTTTATCC GGATCTAATA ATATCCATCT TAGACTTAGC TAAGTTTGGA TCTGTTTTTT
      GCAAAACAGC CTGGAAGAAG GCCAAATAGG CCTAGATTAT TATAGGTAGA ATCTGAATCG ATTCAAACCT AGACAAAAAA

1041  GGTTAGCTCT TGTCAATCGC CTCATCATCA GCAAGAAGGT GAAATTTTTG ACAAATAAAT CTTAGAATCA TGTAGTGTCT
      CCAATCGAGA ACAGTTAGCG GAGTAGTAGT CGTTCTTCCA CTTTAAAAAC TGTTTATTTA GAATCTTAGT ACATCACAGA

1121  TTGGACCTTG GGAATGATAG AAACGATTTG TTATAGCTAC TCTATGTATC AGACCCTGAC CAAGATCCAA CAATCTCATA
      AACCTGGAAC CCTTACTATC TTTGCTAAAC AATATCGATG AGATACATAG TCTGGGACTG GTTCTAGGTT GTTAGAGTAT
```

*FIG. 19B*

```
1201  GGTTTTGTGC ATATGAAACC TTCGACTAAC GAGAAGTGGT CTTTTAATGA GAGAGATATC TAAAATGTTA TCTTAAAAGC
      CCAAAACACG TATACTTTGG AAGCTGATTG CTCTTCACCA GAAAATTACT CTCTCTATAG ATTTTACAAT AGAATTTTCG

1281  CCACTCAAAT CTCAAGGCAT AAGGTAGAAA TGCAAATTTG GAAAGTGGGC TGGGCCTTTT GTGGTAAAGG CCTGTAACCT
      GGTGAGTTTA GAGTTCCGTA TTCCATCTTT ACGTTTAAAC CTTTCACCCG ACCCGGAAAA CACCATTTCC GGACATTGGA

1361  AGCCCAATAT TAGCAAAACC CTAGACGCGT ACATTGACAT ATATAAACCC GCCTCCTCCT TGTTTAGGGT TTCTACGTGA
      TCGGGTTATA ATCGTTTTGG GATCGGCCA TGTAACTGTA TATATTGGG CGGAGGAGGA ACAAATCCCA AAGATGCACT

1441  GAGAGAGCGA AACACAAAAG GATCC                                          Seq. ID No. 13
      CTCTCTCGCT TTGTGTTTTC CTAGG                                          Seq. ID No. 14
                                ─────
                                BamHI
```

FIG. 19C

```
 1  GGATCCACAA ACTTACAAAT TTCTCTGAAG TTGTATCCTC AGTACTTCAA AGAAATAGC TTACACCAAA TTTTTTCTTG
    CCTAGGTGTT TGAATGTTTA AAGAGACTTC AACATAGGAG TCATGAAGTT TCTTTTATCG AATGTGGTTT AAAAAAGAAC
    ─────
    BamHI

81  TTTTCACAAA TGCCGAACTT GGTTCCTTAT ATAGGAAAAC TCAAGGGCAA AAATGACACG GAAAAATATA AAAGGATAAG
    AAAAGTGTTT ACGGCTTGAA CCAAGGAATA TATCCTTTTG AGTTCCCGTT TTTACTGTGC CTTTTTATAT TTTCCTATTC
```

FIG. 21A

```
                                    HindIII
161  TAGTGGGGGA TAAGATTCCT TTGTGATAAG GTTACTTTCC GAAGCTTAGT TGATAAAATA TTTTTATTTG GTTGTAATTT
     ATCACCCCCT ATTCTAAGGA AACACTATTC CAATGAAAGG CTTCGAATCA ACTATTTTAT AAAAATAAAC CAACATTAAA 241  TGTAATATCC CGGGATATTT CACAAATTGA ACATAGACTA CAGAATTTTA GAAAACAAAC TTCTCTCTC TTATCTCACC
     ACATTATAGG GCCCTATAAA GTGTTTAACT TGTATCTGAT GTCTTAAAAG CTTTGTTTG AAAGAGAGAG AATAGAGTGG 321  TTTATCTTTT AGAGAGAAAA AGTTCGATTT CCGGTTGACC GGAATGTATC TTTGTTTTT TTGTTTTGTA ACATATTCG
     AAATAGAAAA TCTCTCTTTT TCAAGCTAAA GGCCAACTGG CCTTACATAG AAACAAAAA AACAAAACAT TGTATAAAGC 401  TTTTCCGATT TAGATCGGAT CTCCTTTTCC GTTTTGTCGG ACCTTCTTCC GGTTATCCG GATCTAATAA TATCCATCTT
     AAAAGGCTAA ATCTAGCCTA GAGGAAAAGG CAAAACAGCC TGGAAGAAGG CCAAATAGGC CTAGATTATT ATAGGTAGAA 481  AGACTTAGCT AAGTTGGAT CTGTTTTTG GTTAGCTCTT GTCAATCGCC TCATCATCAG CAAGAAGGTG AAATTTTGA
     TCTGAATCGA TTCAAACCTA CATCACAGAA CAATCGAGAA CAGTTAGCGG AGTAGTAGTC GTTCTTCCAC TTTAAAAACT 561  CAAATAAATC TTAGAATCAT GTAGTGTCTT TGGACCTTGG GAATGATAGA ACGATTTGT TATAGCTACT CTATGTATCA
     GTTTATTTAG AATCTTAGTA CATCACAGAA ACCTGGAACC CTTACTATCT TTGCTAAACA ATATCGATGA GATACATAGT 641  GACCCTGACC AAGATCCAAC AATCTCATAG GTTTTGTGCA TATGAAACCT TCGACTAACG AGAAGTGGTC TTTTAATGAG
     CTGGGACTGG TTCTAGGTTG TTAGAGTATC CAAAACACGT ATACTTTGGA AGCTGATTGC TCTTCACCAG AAAATTACTC 721  AGAGATATCT AAAATGTTAT CTTAAAAGCC CACTCAAATC TCAAGGCATA AGTAGAAAAT GCAAATTTGG AAGTGGGCT
     TCTCTATAGA TTTTACAATA GAATTTTCGG GTGAGTTTAG AGTTCCGTAT TCCATCTTTA CGTTTAAACC TTCACCCGA
```

*FIG. 21B*

PstI

```
 801  GGGCCTTCTG CAGTTGATAA AATATTTTA TTTGGTTGTA ATTTTGTAAT ATCCCGGGAT ATTTCACAAA TTGAACATAG
      CCCGGAAGAC GTCAACTATT TTATAAAAAT AAACCAACAT TAAAACATTA TAGGGCCCTA TAAAGTGTTT AACTTGTATC

881  ACTACAGAAT TTAGAAAAC AAACTTTCTC TCTCTTATCT CACCTTTATC TTTTAGAGAG AAAAAGTTCG ATTTCCGGTT
      TGATGTCTTA AAATCTTTTG TTTGAAAGAG AGAGAATAGA GTGGAAATAG AAAATCTCTC TTTTTCAAGC TAAAGGCCAA

961  GACCGGAATG TATCTTTGTT TTTTTTGTT TGTAACATAT TTCGTTTTCC GATTAGAGTC AGCTAAGTTT TTCCGTTTTG
      CTGGCCTTAC ATAGAAACAA AAAAAACAA ACATTGTATA AAGCAAAAGG CTAAATCTAG TCGATTCAAA AAGGCAAAAC

1041  TCGGACCTTC TTCCGGTTTA TCCGGATCTA ATAATATCCA TCTTAGACTT AGCTAAGTTT GGATCTGTTT TTTGGTTAGC
      AGCCTGGAAG AAGGCCAAAT AGGCCTAGAT TATTATAGGT AGAATCTGAA TCGATTCAAA CCTAGACAAA AAACCAATCG

1121  TCTTGTCAAT CGCCTCATCA TCAGCAAGAA GGTGAAATTT TTGACAAATA AATCTTAGAA TCATGTAGTG TCTTTGGACC
      AGAACAGTTA GCGGAGTAGT AGTCGTTCTT CCACTTTAAA AACTGTTTAT TTAGAATCTT AGTACATCAC AGAAACCTGG

1201  TTGGAATGA TAGAAACGAT TTGTTATAGC TACTCTATGT ATCAGACCCT GACCAAGATC CAACAATCTC ATAGGTTTTG
      AACCCTTACT ATCTTTGCTA AACAATATCG ATGAGATACA TAGTCTGGGA CTGGTTCTAG GTTGTTAGAG TATCCAAAAC

1281  TGCATATGAA ACCTTCGACT AACGAGAAGT GGTCTTTTAA TGAGAGAGAT ATCTAAAATG TTATCTTAAA AGCCCACTCA
      ACGTATACTT TGGAAGCTGA TTGCTCTTCA CCAGAAAATT ACTCTCTCTA TAGATTTTAC AATAGAATTT TCGGGTGAGT
```

KpnI

*FIG. 21C*

```
1361  AATCTCAAGG CATAAGGTAG AAATGCAAAT TTGGAAAGTG GGCTGGGCCT TGGTACCCGG AAAGTAACCT TATCACAAAG
      TTAGAGTTCC GTATTCCATC TTTACGTTTA AACCTTTCAC CCGACCCGGA ACCATGGGCC TTTCATTGGA ATAGTGTTTC

1441  GAATCTTATC CCCCACTACT TATCCTTTTA TATTTTCCG TGTCATTTTT GCCCTTGAGT TTTCCTATAT AAGGAAGGAA
      CTTAGAATAG GGGGTGATGA ATAGGAAAAT ATAAAAAGGC ACAGTAAAAA CGGGAACTCA AAAGGATATA TTCCTTGGTT

1521  GTTCGGCATT TGTGAAAACA AGAAAAAATT TGGTGTAAGC TATTTTCTTT GAAGTACTGA GGATACAACT TCAGAGAAAT
      CAAGCCGTAA ACACTTTTGT TCTTTTTTAA ACCACATTCG ATAAAAGAAA CTTCATGACT CCTATGTTGA AGTCTCTTTA

BamHI
1601  TTGTAAGTTT GTGGATCC         Seq. ID No. 15
      AACATTCAAA CACCTAGG         Seq. ID No. 16
```

FIG. 21D

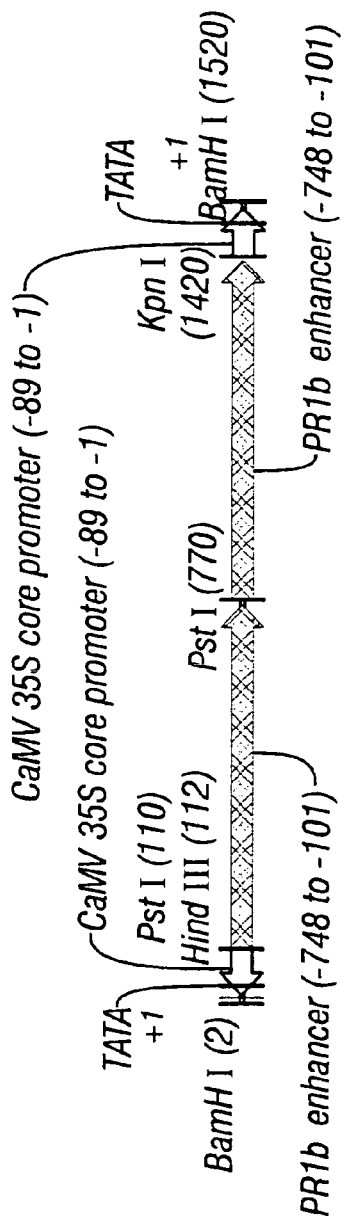

FIG. 22

BamHI

1   GGATCCAGCG TGTCCTCTCC AAATGAAATG AACTTCCTTA TATAGAGGAA GGGTCTTGCG AAGGATAGTG GGATTGTGCG
    CCTAGGTCGC ACAGGAGAGG TTTACTTTAC TTGAAGGAAT ATATCTCCTT CCCAGAACGC TTCCTATCAC CCTAACACGC

PstI       HindIII

81  TCATCCCTTA CGTCAGTGGA GATACTGCAG AAGCTTCAGA CTCATTAACT TAAAAGAAGA TATAGACTCA TTAACTTAAA
    AGTAGGGAAT GCAGTCACCT CTATGACGTC TTCGAAGTCT GAGTAATTGA ATTTTCTTCT ATATCTGAGT AATTGAATTT

161 AGAAGATATA GATTCCAACA CAAGTTCAAA ATTCATAAAC GTCAATCTTG GCTAAATTTC TGAACATCAA TGCATTCCTT
    TCTTCTATAT CTAAGGTTGT GTTCAAGTTT TAAGTATTTG CAGTTAGAAC CGATTTAAAG ACTTGTAGTT ACGTAAGGAA

241 TAAAATATAG ATAATAAGTT AGGATGTTGT CACTTCTTA AAGCATATTC CGACTGAGTC TGGTAGAATC TCATAAACTT
    ATTTTATATC TATTATTCAA TCCTACAACA GTGAAGAAT TTCGTATAAG GCTGACTCAG ACCATCTTAG AGTATTTGAA

321 TAGGCCTTAT CTCTTCAATT AGGCAATTAC TTACCTCCGC TCTACTTTAA GAAAATTCAA TGGAGTACAC CATTATTAAG
    ATCCGGAATA GAGAAGTTAA TCCGTTAATG AATGGAGGCG AGATGAAATT CTTTTAAGTT ACCTCATGTG GTAATAATTC

401 TTCATATAAA AATAAAATTA TATTAATTCT GTCTCTTGTT GGTTCGCTCT ATCTTTTTCT GTTTCCTGC TTCAACCATA
    AAGTATATTT TTATTTTAAT ATAATTAAGA CAGAGAACAA CCAAGCGAGA TAGAAAAAGA CAAAGGACG AAGTTGGTAT

481 ACATATACAA GAACTACATT TCCAAGCTA GATATATCTA ACATGACTGA CTTTGTAAAT TTCTTTTGCC AAGTAAAGA
    TGTATATGTT CTTGATGTAA AGGTTCGAT CTATATAGAT TGTACTGACT GAAACATTTA AAGAAAAGCC TTCAATTCT

FIG. 23A

```
561  AAAAAAATGA TGTTATCCAA ATAATAAAGA GAAAGAGCCC TAATGAAAAA AATGATTTAC TATTAGAGTT GTTCAGCTAA
     TTTTTTTACT ACAATAGGTT TATTATTTCT CTTTCTCGGG ATTACTTTTT TTACTAAATG ATAATCTCAA CAAGTCGATT

641  TCACATCAAT TATGGTTTTC ATCAAGTATG ACTAATGGCG GCTCTTATCT CACGTGATGT GACATTGAAA TTCTTTGACT
     AGTGTAGTTA ATACCAAAAG TAGTTCATAC TGATTACCGC CGAGAATAGA GTGCACTACA CTGTAACTTT AAGAAACTGA

PstI

721  TTAACACTAA TGTCATATGC TTTCAAATTA ATAATCCGAT AAAGCTGCAG ACTCATTAAC TTAAAAGAAG ATATAGACTC
     AATTGTGATT ACAGTATACG AAAGTTTAAT TATTAGGCTA TTTCGACGTC TGAGTAATTG AATTTTCTTC TATATCTGAG

801  ATTAACTTAA AAGAAGATAT AGATTCCAAC ACAAGTTCAA AATTCATAAA CGTCAATCTT GGCTAAATTT CTGAACATCA
     TAATTGAATT TTCTTCTATA TCTAAGGTTG TGTTCAAGTT TTAAGTATTT GCAGTTAGAA CCGATTTAAA GACTTGTAGT

881  ATGCATTCCT TTAAAATATA GATAATAAGT TAGGATGTTG TCACTTTCTT AAAGCATATT CCGACTGAGT CTGGTAGAAT
     TACGTAAGGA AATTTTATAT CTATTATTCA ATCCTACAAC AGTGAAAGAA TTTCGTATAA GGCTGACTCA GACCATCTTA

961  CTCATAAACT TTAGGCCTTA TCTCTTCAAT TAGGCAATTA CTTACCTCCG CTCTACTTTA AGAAAATTCA ATGGAGTACA
     GAGTATTTGA AATCCGGAAT AGAGAAGTTA ATCCGTTAAT GAATGGAGGC GAGATGAAAT TCTTTTAAGT TACCTCATGT

1041 CCATTATTAA GTTCATATAA AAATAAAATT ATATTAATTC TGTCTCTTGT TGGTTCGCTC TATCTTTTTC TGTTTCCTG
     GGTAATAATT CAAGTATATT TTTATTTTAA TATAATTAAG ACAGAGAACA ACCAAGCGAG ATAGAAAAAG ACAAAGGAC
```

*FIG. 23B*

```
1121  CTTCAACCAT AACATATACA AGAACTACAT TTTCCAAGCT AGATATATCT AACATGACTG ACTTTGTAAA TTTCTTTTGC
      GAAGTTGGTA TTGTATATGT TCTTGATGTA AAAGGTTCGA TCTATATAGA TTGTACTGAC TGAAACATTT AAAGAAAACG

1201  CAAGTTAAAG AAAAAAAATG ATGTTATCCA AATAATAAAG AGAAAGAGCC CTAATGAAAA AAATGATTTA CTATTAGAGT
      GTTCAATTTC TTTTTTTTAC TACAATAGGT TTATTATTTC TCTTTCTCGG GATTACTTTT TTTACTAAAT GATAATCTCA

1281  TGTTCAGCTA ATCACATCAA TTATGGTTTT CATCAAGTAT GGCTCTTATC TCACGTGATG TGACATTGAA
      ACAAGTCGAT TAGTGTAGTT AATACCAAAA GTAGTTCATA CCGAGAATAG AGTGCACTAC ACTGTAACTT
                                                 KpnI

1361  ATTCTTTGAC TTTAACACTA ATGTCATATG CTTTCAAATT AATAATCCGA TAAAGGTACC TATCTCCACT GACGTAAGGG
      TAAGAAACTG AAATTGTGAT TACAGTATAC GAAAGTTTAA TTATTAGGCT ATTTCCATGG ATAGAGGTGA CTGCATTCCC
                                                                                    BamHI

1441  ATGACGCACA ATCCCACTAT CCTTCGCAAG ACCCTTCCTC TATATAAGGA AGTTCATTTC ATTTGGAGAG GACACGCTGG
      TACTGCGTGT TAGGGTGATA GGAAGCGTTC TGGGAAGGAG ATATATTCCT TCAAGTAAAG TAAACCTCTC CTGTGCGACC

1521  ATCC      Seq. ID No. 17
      TAGG      Seq. ID No. 18

BamHI
```

FIG. 23C

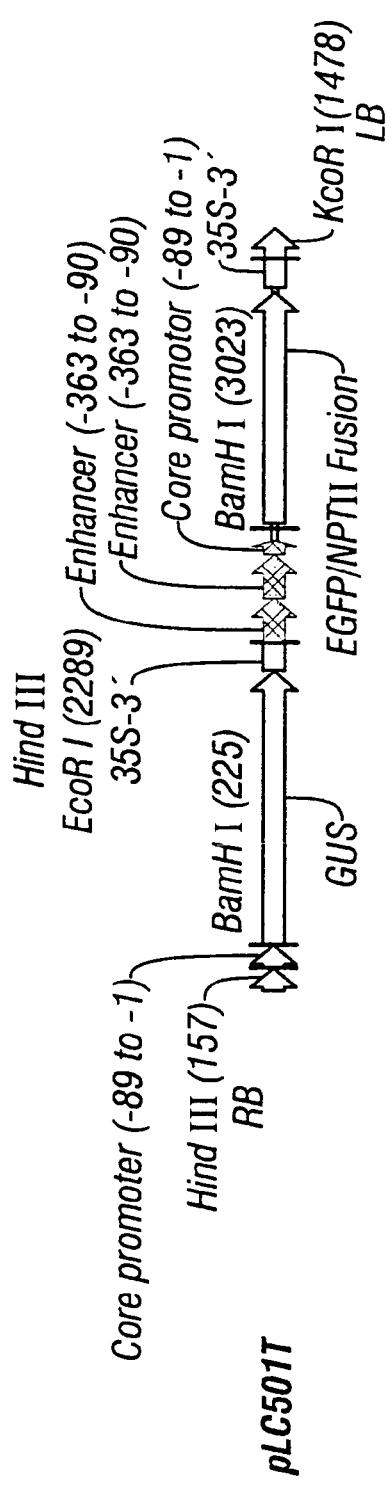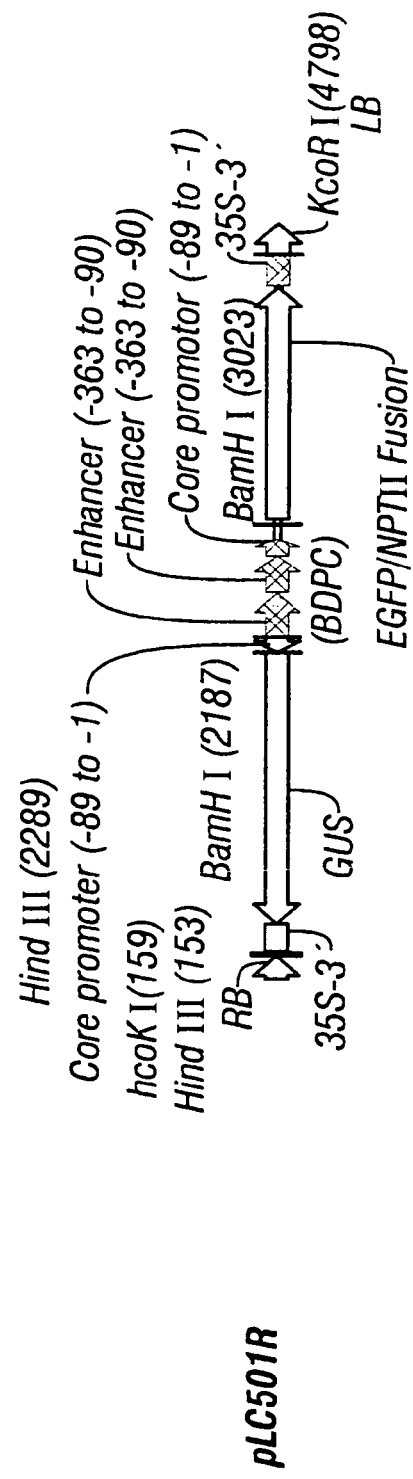
FIG. 24A pLC501T
FIG. 24B pLC501R

BI-DIRECTIONAL DUAL PROMOTER COMPLEX WITH ENHANCED PROMOTER ACTIVITY FOR TRANSGENE EXPRESSION IN EUKARYOTES

The present application is a non-provisional application claiming priority under 35 USC 119(e) to U.S. Provisional Application No. 60/268,358, of Li et al., entitled A BI-DIRECTIONAL DUAL PROMOTER COMPLEX WITH ENHANCED PROMOTER ACTIVITY FOR TRANSGENE EXPRESSION IN EUKARYOTES, filed Feb. 13, 2001, which is incorporated herein in its entirety by reference.

The present invention relates to bidirectional dual promoter complexes (BDPC) for enhancement of transgene expression. More particularly, a BDPC is constructed by placing two core promoters on either side of modified enhancers.

BACKGROUND

Gene expression is composed of several major processes, including transcription, translation and protein processing. Among these processes, transcription not only dictates the precise copying of DNA into mRNA but also provides sophisticated mechanisms for the control of gene expression. There are a number of fundamental steps involved in transcription: promoter recognition and binding by transcription factors and RNA polymerase components, nascent RNA chain initiation, RNA transcript elongation, and RNA transcript termination (Uptain et al., Ann. Rev. Biochem. 66:117–172 (1997)). Promoters are an essential component for transcription, effecting transcription both quantitatively and qualitatively. A promoter contains numerous DNA motifs or cis-elements that can serve as recognition signals and binding sites for transcription factors. Working together with transcription factors, these cis-elements can function as architectural elements or anchoring points for achieving promoter geometry (Perez-Martin et al., Ann. Rev. Microbiol. 51:593–628 (1997)).

Numerous promoters have been isolated from a wide variety of organisms ranging from viruses to animals. They have become the subjects of intensive studies in efforts to characterize their molecular organization and the basic mechanisms regulating transcriptional control of gene expression. In recent years, a number of well-characterized promoters have been successfully adopted for use in the genetic transformation of plants. These promoters control transgene expression in transgenic plants and have been used in efforts to improve agronomic performance and to incorporate value-added features. However, in spite of the availability of these promoters, there is currently a shortage of promoters for use in genetic transformation research with plants. In most instances, use of existing plant promoters isolated from a specific species to effect transformation in a different species results in reduced promoter activity and/or altered patterns of gene expression, reflecting the variation of genetic background between different species (Ellis et al., EMBO J. 6:11–16 (1987); Miao et al., Plant Cell 3:11–22 (1991)). Recently, a constitutive actin gene promoter isolated from *Arabidopsis* (An et al., Plant J. 10:107–121 (1996)) failed to support desired levels of transgene expression in grape cells. To date, the promoter most commonly used to effect transformation in crop plants is the cauliflower mosaic virus 35S (CaMV 35S) promoter and its derivatives (Sanfacon, Can. J. Bot. 70:885–899 (1992)). The CaMV 35S promoter was originally isolated from a plant virus.

Successful genetic transformation of plants frequently requires the use of more than one promoter to adequately drive expression of multiple transgenes. For instance, at least three promoters are normally needed in order to express a selectable marker gene, a reporter marker gene and a target gene of interest. Multiple promoters are required because almost all the mRNAs in eukaryotes are monocistronic (single polypeptide-encoding transcript). Hence, expression of complex traits controlled by more than a single target gene in plants has been thought to require the use of additional promoters.

Recent studies have showed that foreign DNA integrated into the plant genome can be recognized by host factors and that the foreign DNA may be subsequently subjected to modifications that lead to transgene silencing. Mechanisms involved in this process include; DNA methylation, chromatin structural modification and post-transcriptional mRNA degradation (Kumpatla et al., TIBS 3:97–104 (1998)). In general, foreign DNA containing repeated sequences, including sequences homologous to host DNA, is more prone to gene silencing modifications (Selker, Cell 97:157–160 (1999)). Accordingly, the repeated use of the same promoter in transformation vector may increase the probability of gene silencing and unstable transgene expression in transgenic plants. As more transgenic crop plants are developed for release to the farmers, transgene silencing is likely to become a major concern. Hence, there is an urgent need to develop new promoters that will efficiently drive transgene expression, especially in transgenic plants.

Over the years, several strategies have been adopted for use to improve the performance of various promoters. These strategies can be classified into two categories, namely 1) modification of homologous promoters and 2) construction of heterologous promoters.

Modification of homologous promoters is accomplished by manipulating the enhancer region of a particular promoter in an effort to achieve higher transcriptional activity without altering existing expression patterns. Kay et al. (Science 236:1299–1302 (1987) first demonstrated that approximately ten-fold higher transcriptional activity was achieved by tandem duplication of 250 base pairs of the upstream enhancer region of the CaMV 35S promoter, as compared to the transcriptional activity of the natural promoter. Mitsuhara et al. (Plant Cell Physiol. 37:49–59 (1996)) further showed that other forms of tandem repeats of the upstream enhancer region of the CaMV 35S promoter were also capable of producing 10 to 50 fold higher levels of transgene expression in rice and tobacco without altering the constitutive expression pattern of the promoter.

Modification of promoters using heterologous enhancer sequences is also commonly practiced to achieve higher transcriptional activity and desired expression patterns. For example, a CaMV 35S promoter upstream enhancer fragment was fused to the nopaline synthase promoter (NOS) and the resulting fusion promoter reportedly increased the transcriptional activity, as compared to the weaker NOS promoter (Odell, et al. PMB 10:263–272 (1988)). The upstream enhancer regions of the CaMV 35S promoter and the octopine synthase promoter were used to fuse with the maize Adhl promoter to enhance transcription activity, while retaining the anaerobic regulation pattern of the Adhl promoter (Ellis et al. EMBO J.6:11–16 (1987) and 6:3203–3208 (1987)). The achievement of transcriptional enhancement by using heterologous enhancers is primarily attributable to the unique characteristics of enhancers, which could exert its functions to regulate transcriptional activity in an orientation- and position-independent fashion.

SUMMARY

The present invention is directed to a bidirectional dual promoter complex (BDPC) for enhancement of transgene expression and a method for constructing a BDPC. In accordance with the invention, the BDPC includes at least two core promoters and at least one modified internal enhancer region. The core promoters are fused to either end of the modified enhancer region in a divergent orientation such that the transcriptional direction (5' to 3') of each promoter points away from each other (see for example FIG. 1). The modified enhancer region includes at least two tandem oriented enhancer sequences having substantial sequence identity. Each core promoter is capable of independently directing transcription of a transgene that may contain expressible or nonexpressible coding sequences.

In another aspect of the invention, both enhancer and core promoter components used in a BDPC may be derived from homologous and/or heterologous promoter sequences. More specifically, in a homologous BDPC, the repeated enhancer sequences and core promoters may be isolated from a single source promoter that is composed of an enhancer and a core promoter. In a heterologous BDPC, the repeated enhancer sequences may be isolated from a promoter source that is different from that which the source promoter from which the core promoters are obtained.

The core promoter of the present invention includes a DNA sequence that corresponds to about 50 bp to about 100 bp. The core promoter may include a TATA-box consensus element and an Initiator (INR). In another aspect of the invention, the core promoter includes a TATA-box consensus element, an INR, and at least one cis-acting element such as a CAAT-box or an as-1 element (Benfey et al., Science 250:959–966 (1990)). Core promoters in a BDPC may have substantial sequence identity or in one aspect of the invention, be identical. In another aspect, the core promoters of the invention may have a sequence homology of at least about 30% and include at least 5 bp identical, contiguous nucleotides within the core promoter region.

The modified enhancer region in the BDPC may include at least two enhancer sequences having substantial sequence identity arranged in a tandem orientation. In one aspect, the enhancer sequences are identical. The modified enhancer regions are constructed such that the 3' end of a first enhancer sequence is linked to the 5' end of a second enhancer sequence to form a modified enhancer region of the BDPC of the invention. In another aspect, more than two, or multiples of two, such as four and six, repeated enhancer sequences can also be used to construct a BDPC. In an aspect of the invention where four enhancer sequences are used, a first tandem two-unit enhancer region may be fused with another tandem two-unit enhancer region in a back-to-back orientation. The DNA sequence of each enhancer region in a BDPC may be about 100 bp to about 1.0 kbp. In one aspect, transcriptional efficiency is increased when enhancer regions are asymmetrical. The size of an enhancer region is based on desired requirements for the level of transcriptional activity and on desired requirements for a specific transgene expression regulation mechanism.

The modified enhancer region of the BDPC of the invention may also include enhancer sequences that are fully functional to the core promoters used in the BDPC. In this aspect of the invention, enhancers that are fully functional are capable of modulating, including enhancing or down regulating, the initiation and synthesis of transcripts from a transgene containing either translatable or non-translatable coding sequences.

In another aspect, the BDPC of the invention is utilized to provide simultaneous control of transgene transcription and expression from both core promoters whose transcriptional activities are significantly enhanced by the arrangement of the promoter complex. The use of the BDPC of the invention in transgenic hosts is effective for providing enhanced levels of transcription in both transient expression and stable transformation assays. In this aspect of the invention, by using a homologous BDPC that includes two modified enhancer regions and two core promoters, all of which are derived from the same source promoter, up to a 220-fold increase in transcriptional activity was obtained from an upstream core promoter as compared to transcriptional activity from the same core promoter alone (see FIG. 13). Up to a 2-fold increase in transcription activity can be achieved from an upstream core promoter in a BDPC as compared to that same core promoter having the same enhancer sequences but not in a BDPC. Further, transcriptional activity may be increased as much as 40% in a downstream core promoter in a BDPC as compared to a double enhancer with a core promoter.

In another aspect, the present invention is effective for increasing the number of transcription units and for enhancing transcription control based on the use of a limited number of promoter sequences. Since DNA sequences from a single promoter source can be used to construct a homologous BDPC for the expression of two, or more than two in the case of translation fusion, monocistronic transgene sequences, the number of promoters required to express multiple transgenes is reduced by using the BDPC of the invention. In addition, expression of these multiple transgenes is under the control of the same BDPC and regulated simultaneously according to regulatory information encoded within the shared enhancer region and core promoters. Accordingly, the BDPC of the present invention is effective for achieving synchronized expression of complex multigene-controlled quantitative traits loci (QTL), including those responsible for major events of growth and development in crop plants and other higher organisms. In this aspect, the invention provides transgenic plants, asexual cuttings from these plants in certain instances, and seeds from transgenic plants in certain instances, that contain the BDPC of the present invention. The BDPC of the present invention are also effective for reducing transcriptional silencing of transgene expression.

Examples of BDPCs are set forth in FIG. 2 (SEQ. ID. Nos.: 1 and 2), FIG. 4 (SEQ. ID. Nos.: 3 and 4), FIG. 6 (SEQ. ID. Nos.: 5 and 6), FIG. 8 (SEQ. ID. No.: 7 and 8), FIG. 10 (SEQ. ID. No.: 9 and 10) FIG. 12 (SEQ. ID. No.: 11 and 12), FIG. 19 (SEQ. ID. No.: 13 and 14), FIG. 21 (SEQ. ID. No.: 15 and 16), and FIG. 23 (SEQ. ID. No.: 17 and 18).

BRIEF DESCRIPTION OF FIGURES

FIG. 2 shows the nucleotide sequence (SEQ. ID. Nos.: 1 and 2) of the BDPC illustrated in FIG. 1.

FIG. 3 illustrates a BDPC with 4 enhancers based on CaMV 35S promoter.

FIG. 4 shows the nucleotide sequence (SEQ. ID. Nos.: 3 and 4) of the BDPC illustrated in FIG. 3.

FIG. 5 illustrates a BDPC with 2 enhancers based on CsVMV promoter.

FIG. 6 shows the nucleotide sequence (SEQ. ID. Nos.: 5 and 6) of the BDPC illustrated in FIG. 5.

FIG. 8 shows the nucleotide sequence (SEQ. ID. Nos.: 7 and 8) of the BDPC illustrated in FIG. 7.

FIG. 10 shows the nucleotide sequence (SEQ. ID. Nos.: 9 and 10) of the BDPC illustrated in FIG. 9.

FIG. 12 shows the nucleotide sequence (SEQ. ID. Nos.: 11 and 12) of the BDPC illustrated in FIG. 11.

FIG. 13 illustrates a physical map of the T-DNA region of binary vectors containing a BDPC.

FIG. 19 shows the nucleotide sequence (SEQ. ID. Nos.: 13 and 14) of the BDPC illustrated in FIG. 18.

FIG. 21 shows the nucleotide sequence (SEQ. ID. Nos.: 15 and 16) of the BDPC illustrated in FIG. 20.

FIG. 22 illustrates a heterologous BDPC with 2 PR1b enhancers and 2 CaMV 35S core promoters.

FIG. 23 shows the nucleotide sequence (SEQ. ID. Nos.: 17 and 18) of the BDPC illustrated in FIG. 22.

FIG. 24 illustrates a physical map of a T-DNA region of CaMV 35S promoter-derived binary vectors containing a BDPC.

DETAILED DESCRIPTION

Definitions

Figure 1:
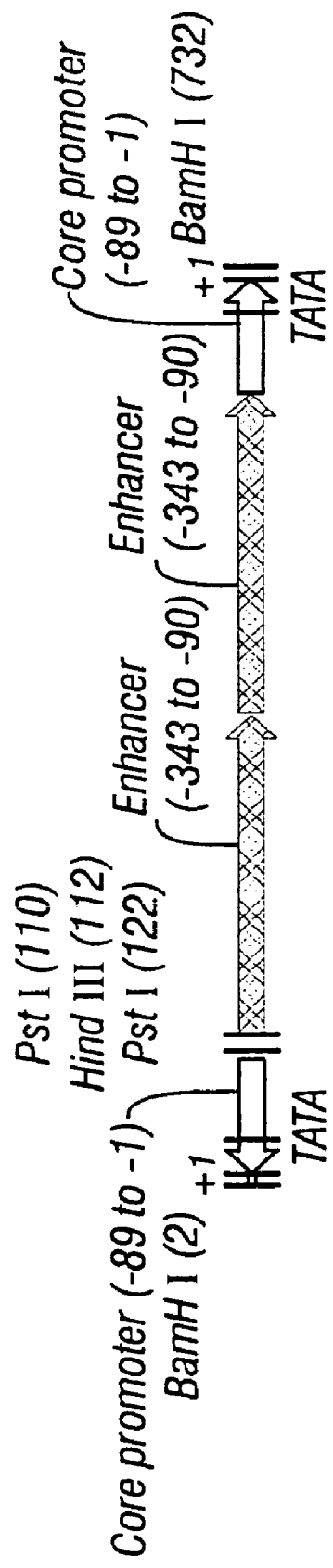
FIG. 1 illustrates a BDPC with 2 enhancers based on CaMV 35S promoter.
Figures 6C, 7:
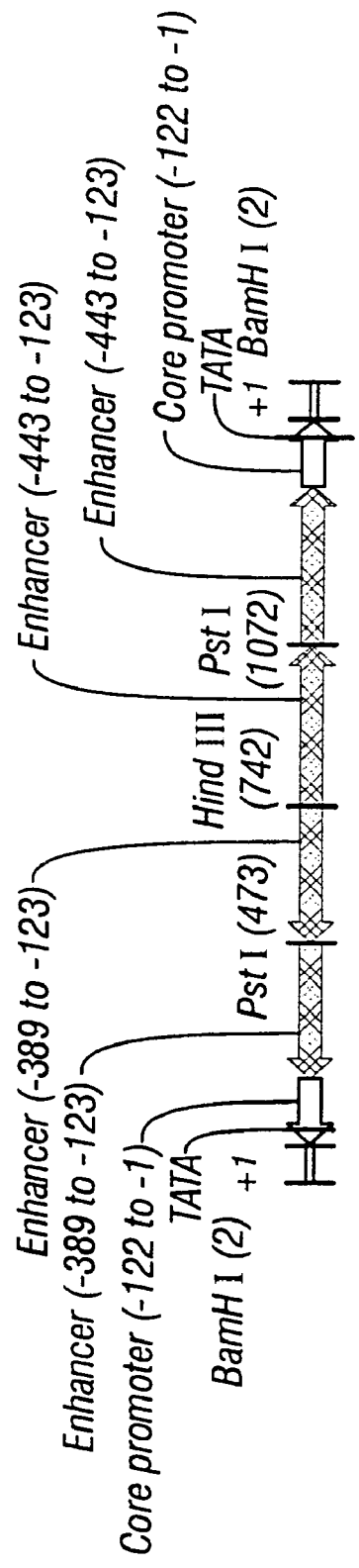
FIG. 7 illustrates a BDPC with 4 enhancers based on CsVMV promoter.
Figure 9:
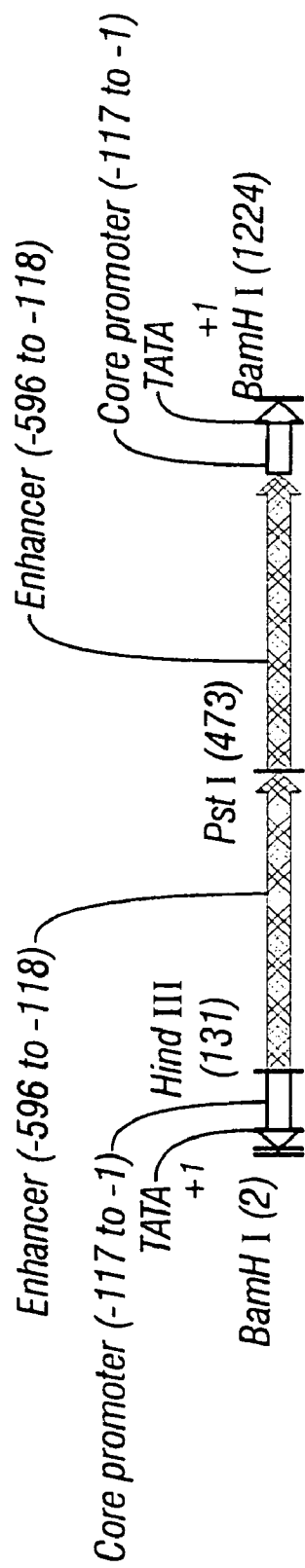
FIG. 9 illustrates a BDPC with 2 enhancers based on ACT2 promoter.
Figure 11:
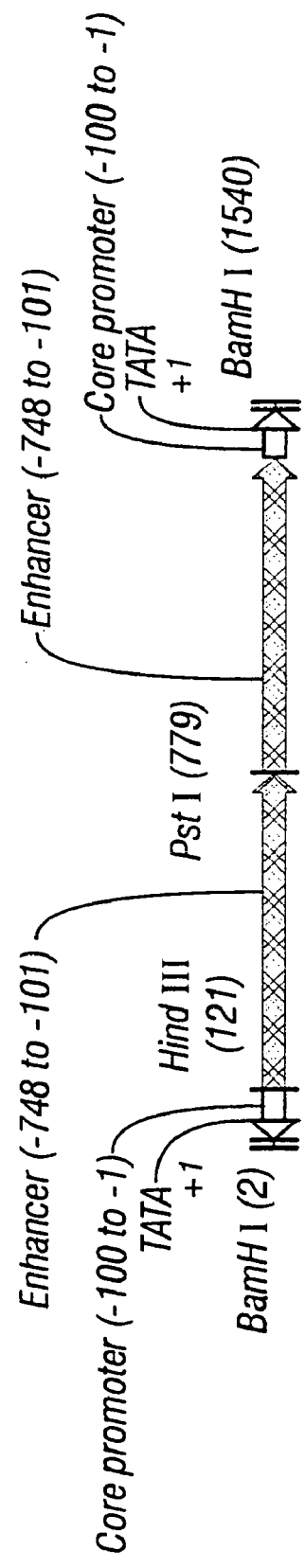
FIG. 11 illustrates a BDPC with 2 enhancers based on PRb1b promoter of tobacco.
Figure 14B:
FIG. 14 illustrates transient GFP expression in grape SE (somatice embryo, *Vitis vinifera* cv. Thompson Seedless) after transformation using binary vectors p201 and p201R.
Figure 14D:
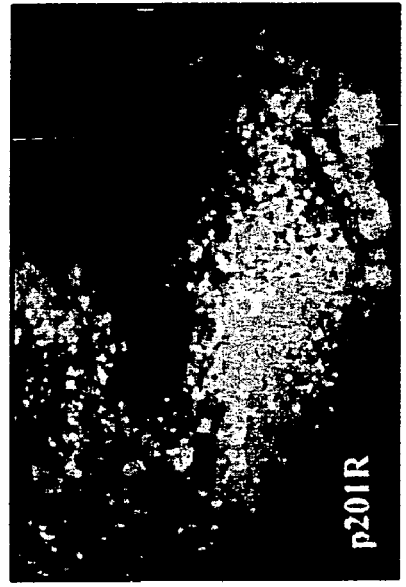
Figure 14A:
Figure 14C:
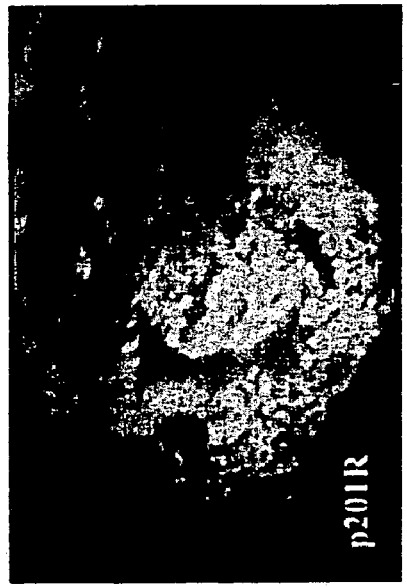

Unless defined otherwise, all technical and scientific terms used herein have the same meaning as commonly understood by one of ordinary skill in the art to which this invention belongs. Singleton et al. (1994) Dictionary of Microbiology and Molecular Biology, second edition, John Wiley and Sons (New York) provides one of skill with a general dictionary of many of the terms used in this invention. All patents and publications referred to herein are incorporated by reference herein. For purposes of the present invention, the following terms are defined below.

The term "nucleic acid" refers to a deoxyribonucleotide or ribonucleotide polymer in either single- or double-stranded form, or sense or anti-sense, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

The terms "operably linked", "in operable combination", and "in operable order" refer to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. In the present application, the gene of interest that is operably linked to the BDPC may be upstream or downstream from the BDPC.

The term "recombinant" when used with reference to a cell indicates that the cell replicates a heterologous nucleic acid, expresses said nucleic acid or expresses a peptide, heterologous peptide, or protein encoded by a heterologous nucleic acid. Recombinant cells can express genes that are not found within the native (non-recombinant) form of the cell. Recombinant cells can also express genes that are found in the native form of the cell, but wherein the genes are modified and re-introduced into the cell by artificial means.

A "structural gene" is that portion of a gene comprising a DNA segment encoding a protein, polypeptide or a portion thereof, and excluding the 5' sequence which drives the initiation of transcription. The structural gene may alternatively encode a nontranslatable product. The structural gene may be one which is normally found in the cell or one which is not normally found in the cell or cellular location wherein it is introduced, in which case it is termed a "heterologous gene". A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications which could effect biological activity or the characteristics, the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bounded by the appropriate splice junctions. The structural gene may be translatable or non-translatable, including in an anti-sense orientation. The structural gene may be a composite of segments derived from a plurality of sources (naturally occurring or synthetic, where synthetic refers to DNA that is chemically synthesized).

"Divergent orientation" refers to an arrangement where sequences are pointing away from each other or in opposite directions in their direction of transcription.

"Derived from" is used to mean taken, obtained, received, traced, replicated or descended from a source (chemical and/or biological). A derivative may be produced by chemical or biological manipulation (including, but not limited to, substitution, addition, insertion, deletion, extraction, isolation, mutation and replication) of the original source.

"Chemically synthesized", as related to a sequence of DNA, means that the component nucleotides were assembled in vitro. Manual chemical synthesis of DNA may be accomplished using well established procedures (Caruthers, *Methodology of DNA and RNA Sequencing*, (1983), Weissman (ed.), Praeger Publishers, New York, Chapter 1);

automated chemical synthesis can be performed using one of a number of commercially available machines.

Two polynucleotides or polypeptides are said to be identical, if the sequence of nucleotides or amino acid residues in the two sequences is the same when aligned for maximum correspondence. Optimal alignment of sequences for comparison may be conducted by the local homology algorithm of Smith and Waterman, Adv. Appl. Math. 2:482 (1981), by the homology alignment algorithm of Needleman and Wunsch, J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The terms "substantial identity" or "substantial sequence identity" as applied to nucleic acid sequences and as used herein denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

Another indication that nucleotide sequences are substantially identical is if two molecules hybridize to each other under stringent conditions. Stringent conditions are sequence-dependent and will be different in different circumstances. Generally, stringent conditions are selected to be about 5° C. to about 20° C., usually about 10° C. to about 15° C., lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For instance in a standard Southern hybridization procedure, stringent conditions will include an initial wash in 6×SSC at 42° C. followed by one or more additional washes in 0.2×SSC at a temperature of at least about 55° C., typically about 60° C. and often about 65° C.

Nucleotide sequences are also substantially identical for purposes of this invention when the polypeptides which they encode are substantially identical. Thus, where one nucleic acid sequence encodes essentially the same polypeptide as a second nucleic acid sequence, the two nucleic acid sequences are substantially identical, even if they would not hybridize under stringent conditions due to silent substitutions permitted by the genetic code (see, Darnell et al. (1990) Molecular Cell Biology, Second Edition Scientific American Books W. H. Freeman and Company New York for an explanation of codon degeneracy and the genetic code).

Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

As used herein, the term "cis" is used in reference to the presence of nucleic acid signal binding elements on a chromosome. The term "cis-acting" is used in reference to the controlling effect of a regulatory nucleic acid element on a gene. For example, enhancers and promoters may include cis acting control elements which may affect transcription.

As used herein, the term "vector" is used in reference to nucleic acid molecules that transfer DNA segment(s) into a cell. A vector may act to replicate DNA and may reproduce independently in a host cell. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eucaryotic cells are known to utilize promoters, enhancers, and termination and polyadenylation signals.

As used herein, the term "TATA element" or "TATA box" is used in reference to a segment of DNA, located approximately 19–27 base pairs upstream from the transcription start point of eucaryotic structural genes, to which RNA polymerase binds. The TATA box is approximately 7 base pairs in length, often comprising as one example, the sequence "TATAAA" or "TATATAA". The TATA box is also sometimes referred to as the "Hogness box."

The term "CAAT box" or "CAAT element" refers to a conserved DNA sequence located upstream from the TATA box or the transcription start point of eucaryotic structural genes, to which RNA polymerase binds.

Transcriptional control signals in eukaryotes comprise "promoter" and "enhancer" elements. Promoters and enhancers consist of short arrays of DNA sequences that interact specifically with cellular proteins involved in transcription (Maniatis, T. et al., Science 236:1237 (1987)). Promoter and enhancer elements have been isolated from a variety of eukaryotic sources including genes in yeast, insect and mammalian cells, plants and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, S. D. et al., Trends Biochem. Sci., 11:287 (1986) and Maniatis, T. et al., supra (1987)).

As used herein the term "transgene" refers to any gene that is not normally present in a particular host.

"Expressible coding sequence", as used herein, refers to a DNA sequence that serves as a template for the synthesis gene products or polypeptides. "Non-expressible coding sequence" refers to any DNA sequences that direct the synthesis of non-translatable transcripts, including antisense mRNA.

Core Promoters

In an important aspect, the BCPC of the present invention includes at least two core promoters. Structurally, the term "core promoter", as used herein, may correspond to, but not limited to, a DNA sequence of about 50 bp to about 100 bp in length. The DNA sequence may contain at least a TATA-box consensus element and the Initiator (INR), and preferably a TATA-box consensus element, the INR and at least one cis-acting element such as the CAAT-box or the as-1 element (Benfey and Chua, Science 250:959–966 (1990)). A core promoter may be commonly isolated from DNA sequences immediately upstream of a transcription start site (TSS) or synthesized chemically according to pre-determined DNA sequence information.

Functionally, the term "core promoter", as used herein, is defined by its capability to direct the precise initiation and synthesis of transcripts from an operably linked nucleic acid sequence at a minimum activity level that can be detected by using currently available gene transcription analysis methods, including reverse transcriptase-polymerase chain reaction assay (RT-PCR), nucleic acid hybridization techniques, DNA-protein binding assays and in vitro and/or in vivo gene expression analysis approaches using living cells (Wefald, et al., Nature 344:260–262 (1990); Benfey and Chua, Science 250:959–966 (1990); Patikoglou and Burley, annu. Rev. Biophys. Biomol. Struct. 26:289–325 (1997)). In one aspect, the core promoters of the invention have a sequence homology where promoter sequences have a homology when compared to each other of at least about 30% and include at least 5 bp identical contiguous nucleotides within the core promoter region.

Both structural and functional features of various core promoters have been previously studied extensively and described in great details in literature (Kollmar and Farnham, Proc. Exp. Biol. Med. 203:127–139 (1993); Orphanides, et al. Genes and Dev. 10:2657–2683 (1996); Roeder, Trends Biochem. Sci. 21:327–335 (1996); Tjian, Philos. Trans. R. Soc. Lond. B. Biol. Sci. 351:491–499 (1996)).

A core promoter is generally referred to as a DNA sequence that is directly located upstream of a nucleic acid sequence that is to be transcribed. However, in a BDPC said nucleic acid sequence may be either upstream or downstream from a core promoter. The nucleic acid sequence to be transcribed may be either translatable or non-translatable and may further include an open reading frame or coding sequence.

The TATA-box and the INR are the two key elements present in a core promoter, both of which play an important role in determining the TSS position and in initiating basal transcription. The consensus sequence for the TATA-box may comprise TATA(A/T)A(A/T) and the INR has the consensus YY$\underline{A}$N(T/A)YY, where the underlined A indicates the TSS. According to observations from numerous cloned gene promoters, abundantly expressed genes generally contain a strong TATA-box in their core promoter, while most housekeeping genes, including oncogenes and those encoding growth factors and transcription factors, may often contain no TATA-box in their core promoter. In some strong core promoters, other cis-acting elements, including the CAAT-box and the as-1 element, are frequently found to be overlapped within the core promoter DNA sequence. For instance, the core promoter of the CaMV 35S promoter was defined experimentally to be a sequence ranging from +1 to −90. This fragement contains the TATA-box consensus (TATATAA), two CAAT-box elements and two as-1 elements (Fang, et al. Plant Cell 1:141–150 (1989); Benfey, et al. EMBO J.9:1677–1684 (1990); Benfey and Chua, Science 250:959–966 (1990)).

Core promoters have a unique structure and organization at the DNA level. Core promoters in a BDPC may have substantial sequence identity or in one aspect of the invention, be identical. In another aspect, the core promoters of the invention have a sequence homology where promoter sequences have a homology of at least about 30% and include in separate aspects of the invention, at least 5, 10 or 20 bp identical contiguous nucleotides within the core promoter region. In another aspect, the core promoters have a sequence homology where promoter sequences have a homology of at least about 40% and include in separate aspects of the invention, at least 5, 10 or 20 identical contiguous nucleotides within the core promoter region. In another aspect, the core promoters have a sequence homology where promoter sequences have a homology of at least about 50% and include in separate aspects of the invention, at least 5, 10 or 20 identical contiguous nucleotides within the core promoter region.

Studies of protein-DNA interactions indicated that the DNA sequence for a core promoter provides critical binding elements and anchoring points essential for the formation of a productive transcription initiation subcomplex that comprises the RNA polymerase II (RNAPII), numerous transcription factors (TFIIA, TFIIB, TFIID, CIFs, TAFs) and the TATA-binding protein (TBP) (see review by Zhang, Genome Res. 8:319–326 (1998)). Accordingly, it is easily recognized that a core promoter is one of the prerequisite components in the transcriptional machinery and plays an important role in supporting the precise initiation and synthesis of transcripts.

Sources of core promoters include but are not limited to CaMV 35S, CsVMV, ACT2, PRB1B, octopine synthase promoter, nopaline synthase promoter, manopine synthetase promoter, beta-conglycinin promoter, phaseolin promoter, ADH promoter, heat-shock promoters, developmentally regulated promoters, and tissue specific promoters.

Modified Enhancer Complex

The present invention includes a modified enhancer region, to which two core promoters are fused upstream and downstream thereof to form a BDPC. In another aspect of the invention, the enhancer sequences may have substantial sequence identity or may in one aspect include at least two identical enhancer sequences that are arranged in a tandem orientation. Alternatively, the enhancers of the invention have a sequence homology where enhancer sequences have a homology of at least about 30% and include at least 5 bp identical contiguous nucleotides within the enhancer sequence. More specifically, the 3' end of the first enhancer sequence is linked to the 5' end of the second sequence to form a modified enhancer region in a BDPC.

In yet another aspect of the present invention, each repeated enhancer sequence in a modified enhancer region may correspond to a DNA sequence of about 100 bp to more than about 1.0 kbp in length. The choice for a particular repeat size is preferably based on the desired transcriptional enhancement and the desired requirements for a specific transgene expression pattern controlled by a particular set of cis-acting elements contained within the enhancer DNA sequence.

In yet another aspect, within a modified enhancer region there may be any number of cis-acting elements that are fully functional to the core promoters used in a BDPC. The cis-acting elements are functional, meaning capable of modulating, including enhancing or down-regulating, the initiation and synthesis of transcripts from a transgene containing either expressible or non-expressible coding sequences.

A modified enhancer region in a BDPC as used herein, may comprise at least two, more than two, or multiple of two, such as four and six, repeated enhancer sequences. If four enhancer repeat sequences are to be used to form a four-unit modified enhancer region in a BDPC, two enhancer sequences are first placed in tandem to form one enhancer array. Two different enhancer arrays made from a total of four repeat sequences will be then fused together in an opposite or back-to-back orientation. More specifically, transcription in the upstream direction may occur on the bottom strand whereas transcription in the downstream direction may occur on the top strand. Likewise, in the case where six enhancer sequences are to be chosen to construct a six-unit modified enhancer region in BDPC, three sequences are first arranged to form an array of tandem repeats. The two different enhancer arrays are finally fused together in a back-to-back orientation to form a six-unit modified enhancer region for use in a BDPC.

The sequence length of all repeated enhancer sequences within one enhancer array may be asymmetrical. As used herein, asymmetrical means that enhancer sequences are at least 10 bp either longer or shorter than the unit length of the enhancer units within the other enhancer array, as used in either a four- or six-unit modified enhancer region. The use of asymmetric enhancer arrays in a four- or six-unit modified enhancer region is preferred to prevent the formation of a perfect palindromic sequence containing overly long (>100 bp) repeated sequences, which may affect stability during DNA manipulation and cloning processes (Allers and Leach, J. Mol. Biol. 252:72–85 (1995); Nasar et al., Mol. Cell. Biol. 20:3449–3458 (2000)).

The term "enhancer" has been previously defined (Khoury and Gruss, Cell 33:313–314 (1983) and extensively used to describe any DNA sequence with a size ranging from approximately 100 bp to over 2.0 kbp. According to studies of eukaryotic promoters, enhancers are commonly isolated from sequences located upstream or downstream of a core promoter and contain numerous cis-acting elements important for transcription regulation. In an important aspect, enhancers function to modulate, including either enhance or limit, the transcriptional activity of the core promoter in an orientation- and/or position-independent fashion. Transcriptional control or regulation of temporal- and spatial-specific gene expression in all eukaryotes is primarily associated with the presence of functional cis-acting elements within enhancers and is the results of interplay between these regulatory elements and cellular factors in host cells.

Over the years, numerous enhancers have been isolated form organisms ranging from viruses to higher mammals. For instance, in higher plants enhancers regulating gene expression in vegetative tissues, xylem and vascular tissues, roots, flowers, fruits and seeds, as well as gene expression in response to biotic and abiotic stresses, have been isolated and well characterized (see reviews by Edwards and Coruzzi, Annu Rev. Genet. 24:275–303 (1990); Guilfoyle, Genetic Engineering Vol. 19, pps. 15–47 (1997)). Many of these isolated enhancers have been utilized in efforts to provide regulated control of transgene expression in host and non-host organisms.

Accordingly, in an important aspect of the present invention, all enhancers isolated thus far can be utilized to construct a modified enhancer region for use in a BDPC to effect transgene expression based on the regulatory information contained in the enhancer of choice. Functional enhancers that are chemically synthesized based on predetermined sequence information may also be used in the construction of a modified enhancer region as described in the present invention. The use of repeated enhancers in a modified enhancer region does not alter the gene expression pattern, but primarily provides a unique means to achieve transcriptional enhancement.

DNA can undergo dynamic conformational changes under many circumstances. Certain types of DNA sequences, including tandem repeats, reversed repeats, repetitive sequence arrays, and symmetrical or asymmetrical palindromic sequences, are conducive to the formation of so-called alternative DNA conformations, such as DNA bending, cruciform structures, DNA loops, DNA haripins, DNA 4-way junction structures, DNA triplexes and so forth (Perez et al., Ann. Rev. Microbiol. 51:593–628 (1997); Selker, Cell 97:157–160 (1999); Gaillard et al., BMC Biochem and Struct. Biol. 1:1 (2000); Caddle et al., J. Mol. Biol. 211:19–33 (1990); Courey et al. J. Mol. Biol. 202:35–43 (1988); Spink et al. PNAS 92:10767–10771 (1995); Moore et al. PNAS 96:1504–1509 (1999); Collin et al. NAR 28:3381–3391 (2000)). In some cases, alternative DNA conformations can be derived from intrinsic bonding interactions between nucleic acid residues contained in a unique DNA sequence; in other cases, they may be induced and/or augmented by the interplay between DNA sequence elements and DNA-binding factors (Pil et al. PNAS 90:9465–9 (1993); Wolfe et al. Chem Biol. 2:213–221 (1995); Slama-Schwok et al. NAR 25:2574–81 (1997)). Alternative DNA conformations within eukaryotic enhancers and promoters have been demonstrated to provide important architectural elements, complex signal interaction devices and efficacious molecular environments for DNA-protein interactions that may result in the formation of productive transcriptional machinery (Perz et al. Ann. Rev. Microbiol. 51:593–628 (1997)).

In one aspect, the present invention is intended to introduce into a BDPC an enhancer region modified to contain two tandem repeat(s) of substantially identical enhancer sequences and two core promoters with a high degree of sequence homology placed in opposite orientation on either side of the modified enhancer region. Although any particular helical structure or alternative conformation associated with a BDPC of the present invention needs to be determined by using molecular techniques available in the art, the significant enhancement of transcriptional activity observed from the use of a BDPC suggests the involvement of unique DNA structural geometry that provides a favorable molecular environment for productive interactions between DNA sequence elements within enhancer and core promoters and transcriptional factors present in host cells. Such interactions eventually lead to the onset of synergistically improved transcription from both core promoters.

Transgene Silencing

In another important aspect, the BDPC of the present invention is effective for decreasing the occurrence of gene silencing resulting from loss of promoter function due to methylation and the like. Changes in DNA structure can trigger the onset of gene silencing. Multiple copies of a gene and inverted gene repeats are vulnerable to DNA methylation modifications that lead to transcriptional silencing (Selker, Cell 97:157–160 (1999)). Tandem repeats of integrated genes can be recognized and modified at the DNA level by host factors (Finnegan et al., Annu. Rev. Plant Physiol. Plant Mol. Biol. 49:223–247 (1998): Kumpatla et al., TIBS 3:97–104 (1998)). A cruciform structure derived from DNA repeats is effectively modified by a mammalian methyltransferase (Smith et al., J. Mol. Biol. 243:143–151 (1994)). However, many cases of transgene silencing derived from repeated sequences involves coding regions (Selker, Cell 97:157–160 (1999); Finnegan et al., Annu. Rev. Plant Physiol. Plant Mol. Biol. 49:223–247 (1998)). BDPCs of the present invention support stable and high levels of transgene expression even though repeated DNA sequences were present within the BDPC region.

Use of BDPCs

In another aspect of the invention, vectors that include a BDPC as described in this invention can be used to express foreign genes in mammalian cells and especially in plant cells that include dicots and monocots. More specifically, dicots include but are not limited to tobacco, grapes, soybeans, legumes, rapeseed, cotton, sunflower, tomatoes, potatoes, sugar beets, alfalfa, cloves and peanuts. Monocots include but are not limited to maize, wheat, sorghum, oats, rye, barley, rice, millets, sugar cane and grasses.

Several techniques exist for introducing foreign genetic material into plant cells, and for obtaining plants that stably maintain and express the introduced gene. Such techniques include acceleration of genetic material coated onto microparticles directly into cells (U.S. Pat. No. 4,945,050 to Cornell and U.S. Pat. No. 5,141,131 to DowElanco). Plants may be transformed using Agrobacterium technology, see U.S. Pat. No. 5,177,010 to University of Toledo, U.S. Pat. No. 5,104,310 to Texas A&M, European Patent Application 0131624B1, European Patent Applications 120516, 159418B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to MaxPlanck, European Patent Applications 604662 and 627752 to Japan Tobacco, European Patent Applications 0267159, and 0292435 and U.S. Pat. No. 5,231,019 all to Ciba Geigy, U.S. Pat. Nos. 5,463,174 and 4,762,785 both to Calgene, and U.S. Pat. Nos. 5,004,863 and 5,159,135 both to Agracetus. Other transformation technology includes whiskers technology, see U.S. Pat. Nos. 5,302,523 and 5,464,765 both to Zeneca. Electroporation technology has also been used to transform plants, see WO 87/06614 to Boyce Thompson Institute, U.S. Pat. Nos. 5,472,869 and 5,384,253 both to Dekalb, WO9209696 and WO9321335 both to PGS. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques within the skill of an artisan.

Foreign genetic material introduced into a plant may include a selectable marker. The preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which code for resistance or tolerance to glyphosate; hygromycin; methotrexate; phosphinothricin (bar); imidazolinones, sulfonylureas and triazolopyrimidine herbicides, such as chlorosulfuron; bromoxynil, dalapon and the like.

In addition to a selectable marker, it may be desirous to use a reporter gene. In some instances a reporter gene may be used without a selectable marker. Reporter genes are genes which are typically not present or expressed in the recipient organism or tissue. The reporter gene typically encodes for a protein which provide for some phenotypic change or enzymatic property. Examples of such genes are provided in K. Weising et al. Ann. Rev. Genetics, 22, 421 (1988), which is incorporated herein by reference. Preferred reporter genes include without limitation glucuronidase (GUS) gene and GFP genes.

Once introduced into the plant tissue, the expression of the structural gene may be assayed by any means known to the art, and expression may be measured as mRNA transcribed, protein synthesized, or the amount of gene silencing that occurs (see U.S. Pat. No. 5,583,021 which is hereby incorporated by reference). Techniques are known for the in vitro culture of plant tissue, and in a number of cases, for regeneration into whole plants (EP Appln No. 88810309.0). Procedures for transferring the introduced expression complex to commercially useful cultivars are known to those skilled in the art.

Once plant cells expressing the gene under control of a bidirectional promoter are obtained, plant tissues and whole plants can be regenerated therefrom using methods and techniques well-known in the art. The regenerated plants are then reproduced by conventional means and the introduced genes can be transferred to other strains and cultivars by conventional plant breeding techniques.

The following examples illustrate methods for carrying out the invention and should be understood to be illustrative of, but not limiting upon, the scope of the invention which is defined in the appended claims.

EXAMPLES

Example 1

Preparation of Transformation Vectors

Two transformation vectors were constructed as illustrated in FIG. 13. Firstly, a green fluorescent protein (GFP) expression cassette was constructed. This cassette was composed of an EGFP (Clontech Laboratories, Inc., Palo Alto, Calif.) under the control of a core promoter (−90 to +1) (Benfey et al., Science 250:959–966 (1989)), and the terminator and polyadenylation signal of CaMV 35S transcript. This expression cassette was then isolated as a HindIII fragment and inserted into the 5' HindIII site of the T-DNA region of a binary vector pBI434 (Li et al., Transgenic Crop I. Biotechnology in Agriculture and Forestry, vol. 46 (1999)). This binary vector contained a GUS-NPTII fusion gene (Dalta et al., Gene 101:239–246 (1991)) under the control of an enhanced double CaMV 35S promoter (Kay et al., Science 236:1299–1302 (1987)) followed by a 5' non-translated leader sequence of alfalfa mosaic virus (AMV) and with a terminator and polyadenylation signal of the nopaline synthase gene of Agrobacterium. Two transformation vectors were obtained depending on the orientation of insertion. In vector p201, the GFP expression cassette was in a tandem orientation relative to the GUS-NPTII expression unit. Secondly, the GFP expression cassette in vector p201R was in a divergent orientation leading to the formation of a BDPC in this vector. In the BDPC, two identical core promoters of the CaMV 35S transcript were located on either side of a duplicated enhancer region [2× (−363 to −91)] resulting in a total size of 736 bp in length (FIG. 2).

Example 2

Transformation of Somatic Embryos of Grape

Binary vectors p201 and p201R were both introduced into A. tumefaciens strain EHA105 and subsequently used to transform somatic embryos (SE) of grape (Vitis vinifera cv.

Thompson Seedless). Expression of the EGFP gene was monitored after transformation using a stereomicroscope equipped with a fluorescence illuminator and GFP filter system. GUS expression was quantitatively determined by using a fluorogenic assay as described by Jefferson (Plant Mol. Biol. Rep. 5:387–405).

As shown in FIG. 14, the differential effects of vectors p201 and p201R on the level of GFP expression were readily noticeable one week after transformation. SE transformed with p201 fluoresced only slightly, while SE transformed with p201R fluoresced brightly. Microscopic observation of the SE revealed that the density of GFP-expressing cells on the surface of transformed SE was similar for both vector treatments. These results indicated that the observed difference in the level of GFP expression between these two vectors was the result of the difference in strength of the promoters used to control EGFP gene expression (FIG. 13). The reduced level of GFP expression in SE following transformation with p201, as opposed to p201R, suggests that the transcriptional activity of the same core promoter can be dramatically increased by using a BDPC.

Figure 15:
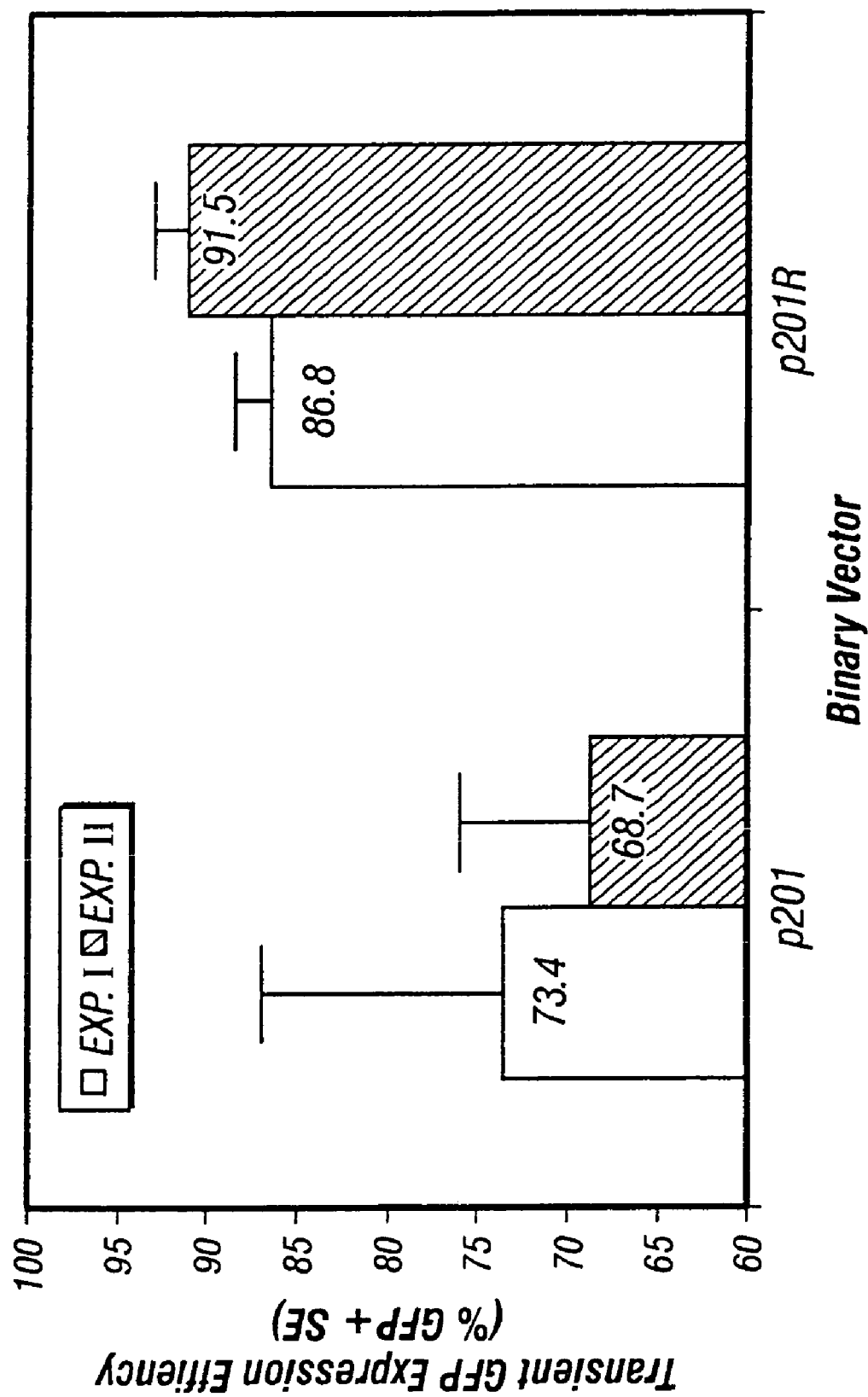
FIG. 15 shows transient GFP expression efficiency of grape SE (*Vitis vinifera* cv. Thompson Seedless) after transformation using binary vectors p201 and p201R.

In addition to enhancing gene expression, use of BDPC increased transformation efficiency based on assays of transient GFP expression (FIG. 15). In two independent experiments, transformation using p201R resulted in an increase of about 19% and about 44%, respectively, in the number of GFP-expressing SE, when compared to p201.

Figure 16A:
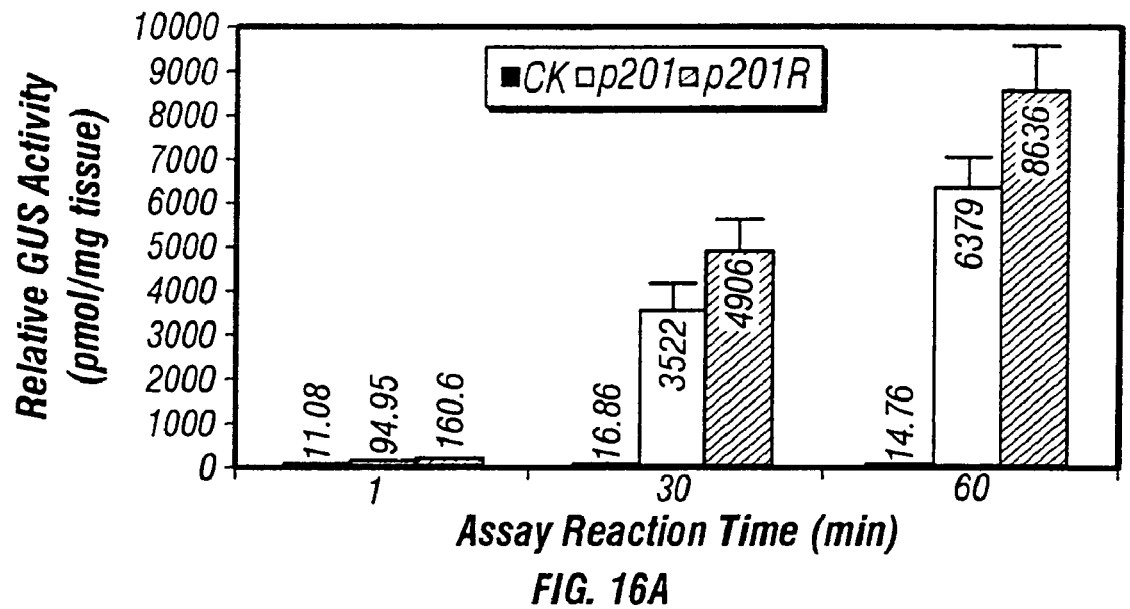
FIG. 16 shows an analysis of GUS activity in grape SE (*Vitis vinifera* cv. Thompson Seedless) after transformation using binary vectors p201 and p201R.
Figure 16B:
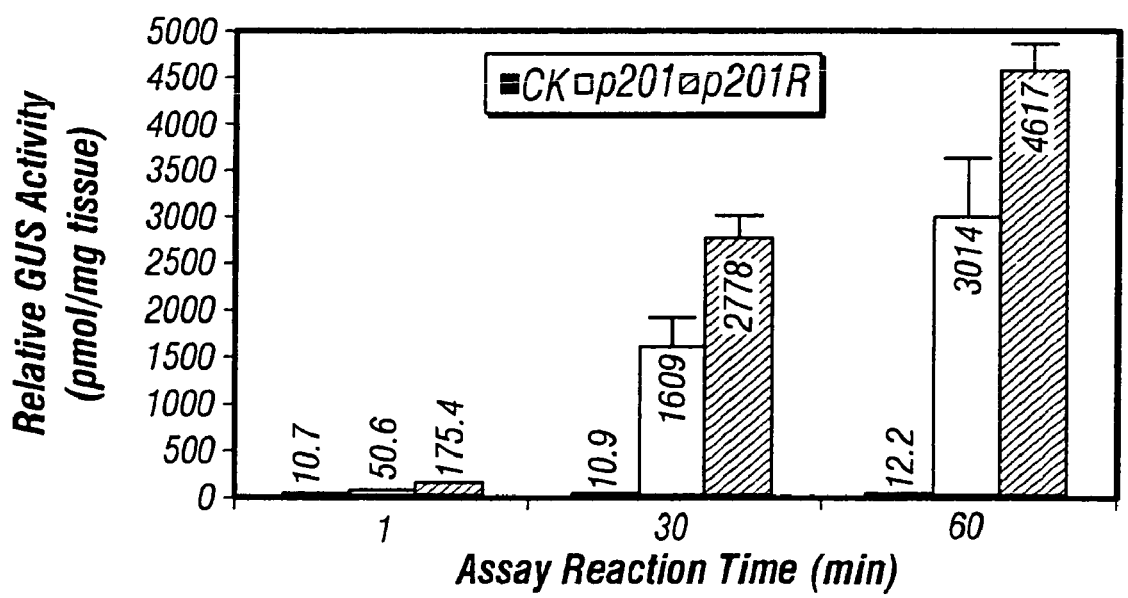

To examine the effect of the BDPC on the downstream core promoter, GFP-expressing SE were selected and further analyzed for GUS expression using a fluorogenic assay. The results illustrated in FIG. 16 indicate that GUS activity in SE transformed using p201R was consistently about 40% higher than the GUS activity detected in SE transformed using p201.

Figure 17A:
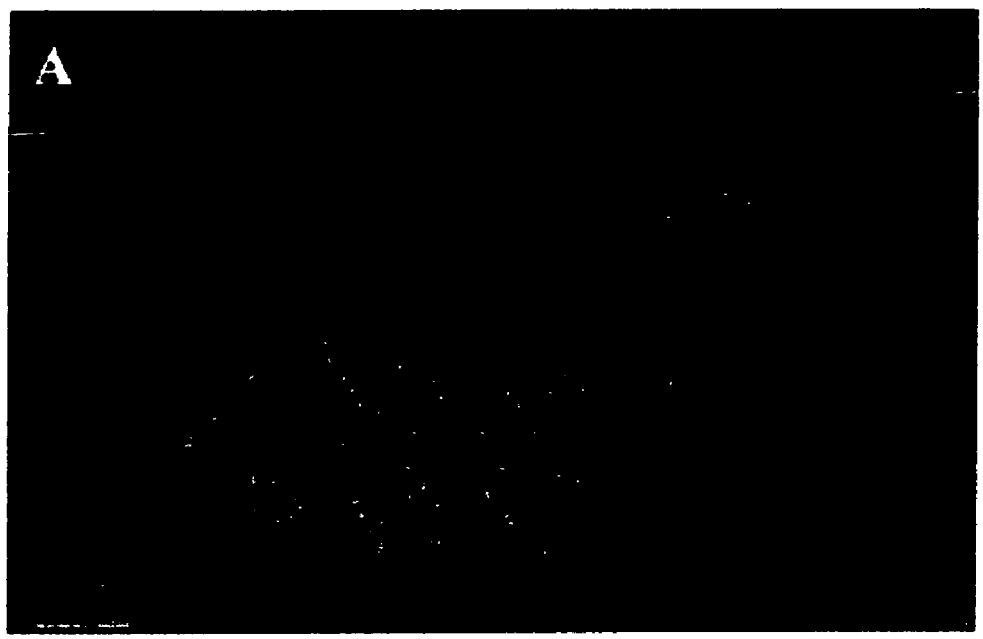
FIG. 17 illustrates GFP expression in grape SE(A) and leaf tissue (B) of transgenic grape (*Vitis vinifera* cv. Thompson Seedless) containing the T-DNA of p201R.
Figure 17B:
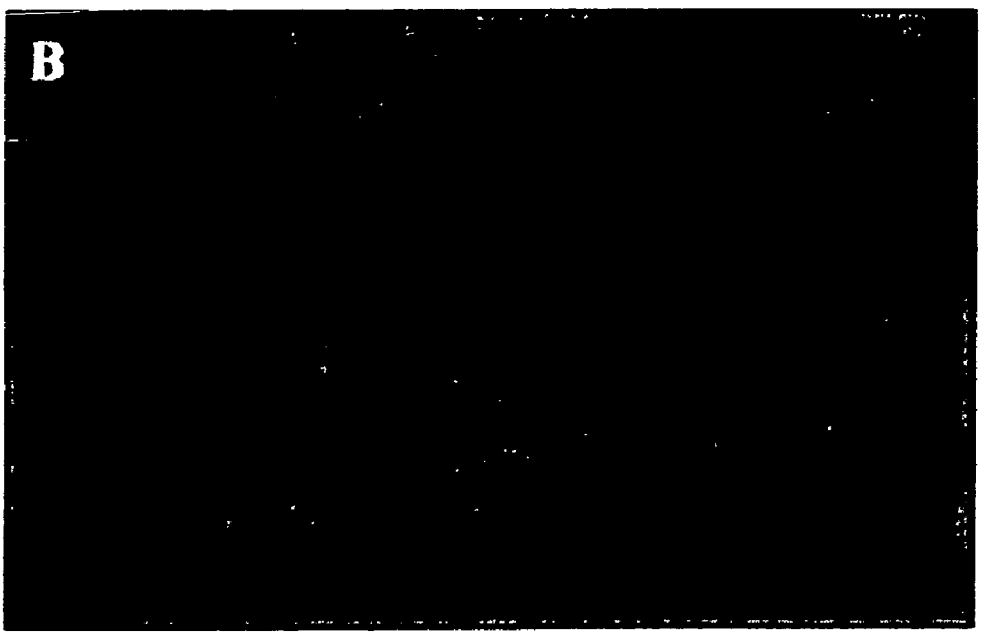
Figure 18:
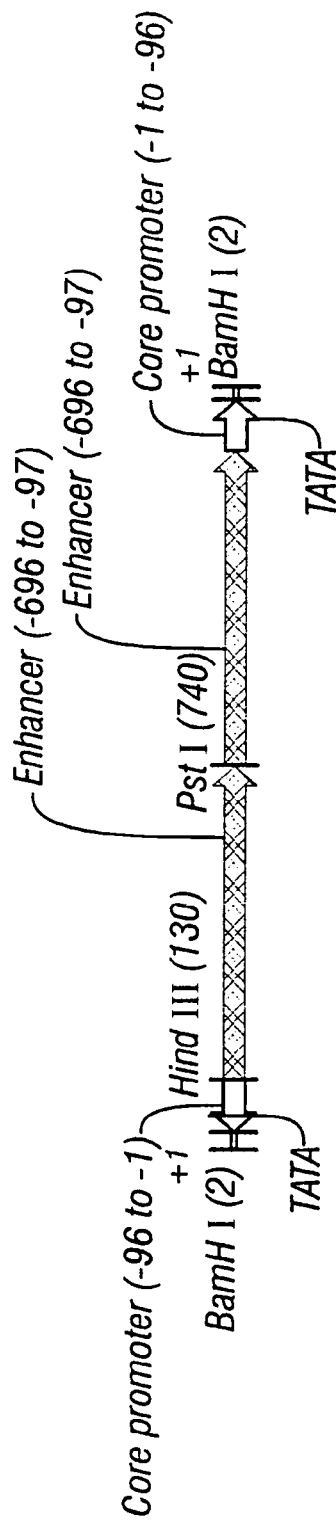
FIG. 18 illustrates a BDPC with 2 enhancers based on At UBQ1 promoter.
Figure 20:
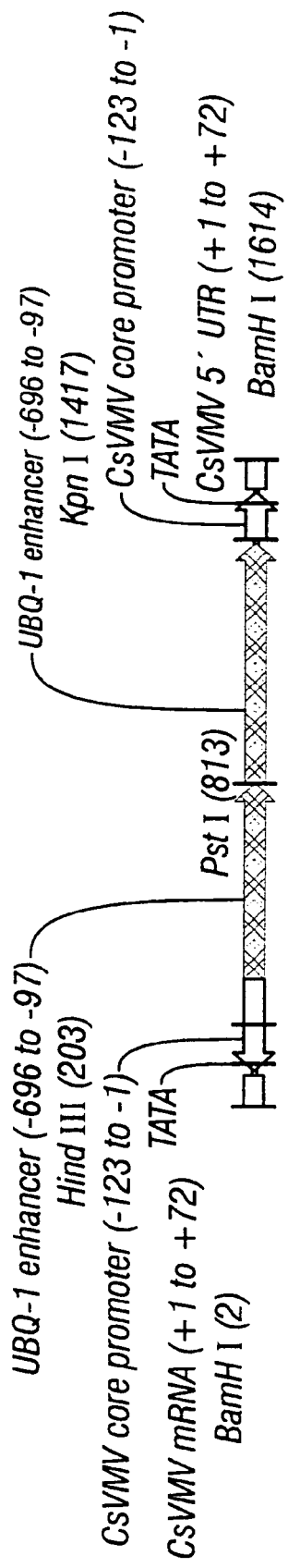
FIG. 20 illustrates a heterologous BDPC with 2 UBQ-1 enhancers and 2 CsVMV core promoters.

Transgenic embryos and plants were subsequently recovered from the SE transformed using p201R. A consistently high level of GFP expression was observed throughout their subsequent developmental stages and in various plant tissues (FIG. 17), with a similar gene expression pattern achieved by using the CaMV 35S promoter as reported previously (Benfey et al., Science 250:959–966 (1989)). This suggests that the induced enhanced gene expression is spatially and temporally stable in transgenic grape plants.

Experimental data obtained indicate that the BDPC present in p201R is capable of significantly elevating the level of expression of both transgenes (EGFP and GUS), as compared to that obtained using p201, which contains a conventional promoter/transgene configuration. This gene expression enhancement is possibly attributable to an improvement in the structural configuration of the BDPC that results in increased promoter activity.

The addition of a second core promoter to the upstream region of the double promoter in a tandem orientation relative to the downstream core promoter, in p201 constituted an array of tandem repeats of promoter sequences within the T-DNA which induces gene silencing (Kumpatla et al., TIBS 3:97–104 (1998)).

Example 3

Quantification of Transgene Expression

To determine quantitatively the transgene expression under control of the upstream core promoter in a BDPC as described in the invention, transformation vectors pLC501T and pLC501R were constructed. As illustrated in FIG. 24, the T-DNA regions of both pLC501T and pLC501R were essentially identical to that of pLC201 and pLC201R, respectively, as shown in FIG. 13, except that the positions of the GUS gene and the EGFP/NPTII gene were switched around, and both transgenes were fused to the terminator of CaMV 35S transcript.

Figure 25:
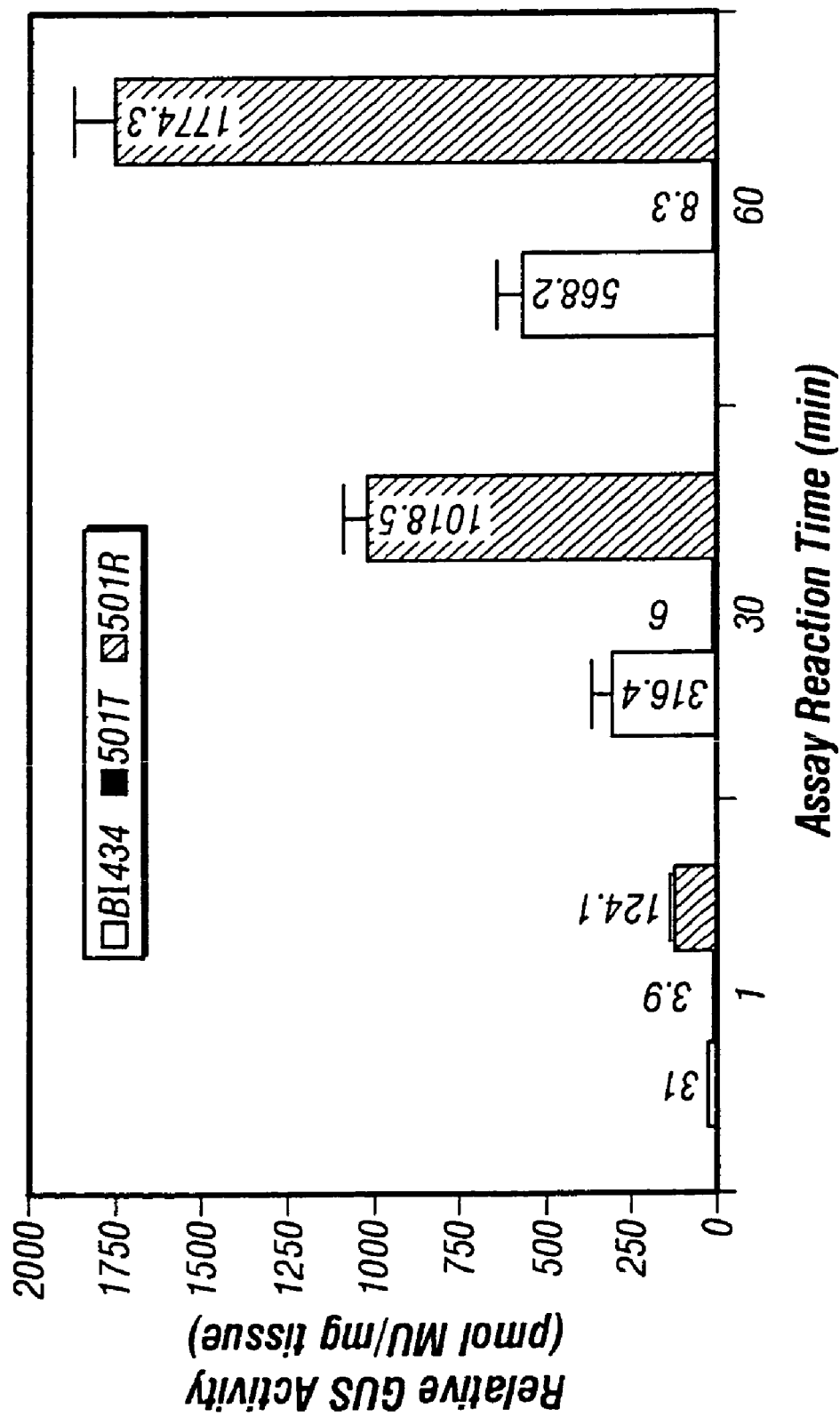
FIG. 25 shows the analysis of GUS activity in three different grape SE (*V. Vinifera* cv. Thompson Seedless) lines after transformation using three binary vectors.

Both pLC501T and pLC501R were introduced into *A. tumefaciens* and subsequently used in transformation of grape SE (cv. Thompson Seedless) as described in Example 2. In this experiment, transformation vector pBI434 containing no BDPC but a GUS/NPTII fusion gene under control of an enhanced double CaMV 35S promoter was also included for GUS activity comparison. FIG. 25 shows GUS activity in SE transformed with various vectors. Noticeably, the core promoter in pLC501T only supported a minimum level of GUS expression (8 pmol MU/mg for 60 min), while a huge increase in GUS expression was observed from SE transformed with pLC501R (1774 pmol MU/mg for 60 min). In other words, up to 220-fold increase in GUS activity was achieved by using pLC501R in which the GUS gene was under the control of the upstream core promoter in a BDPC setting, as compared to the GUS activity derived from the same core promoter without a BDPC configuration (pLC501T). In addition, the GUS activity derived from the upstream core promoter of the BDPC in pLC501R increased by 2-fold, as compared to GUS activity resulted from pBI434, which only contained an enhanced double CaMV 35S promoter. These data, together with observations described in Example 2, clearly demonstrate that a BDPC as described in the invention is effective for achieving stable and significantly high levels of transgene expression enhancement from both core promoters.

Example 4

Quantification of Transgene Expression Under 4-Enhancer-Containing BDPC

Figure 26A:
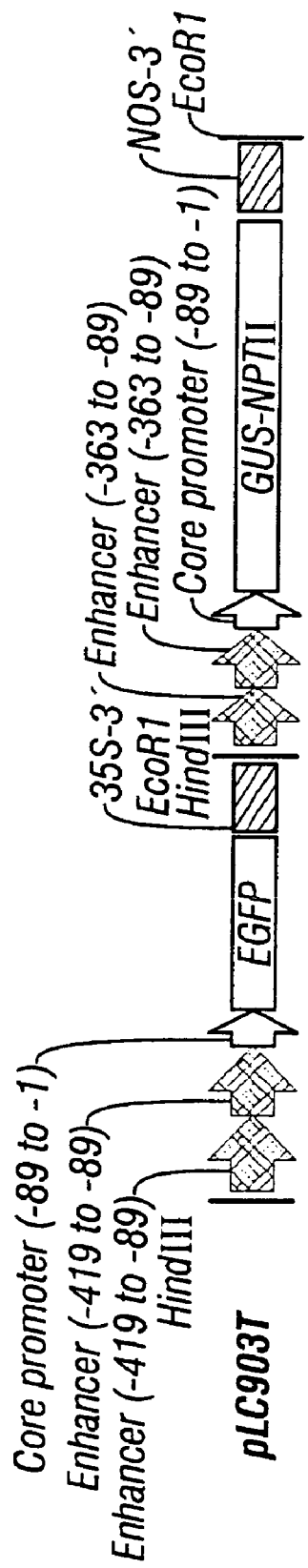
FIG. 26 illustrates a physical map of a T-DNA region of transformation vectors with 4-enhancer-containing BDPC.
Figure 26B:
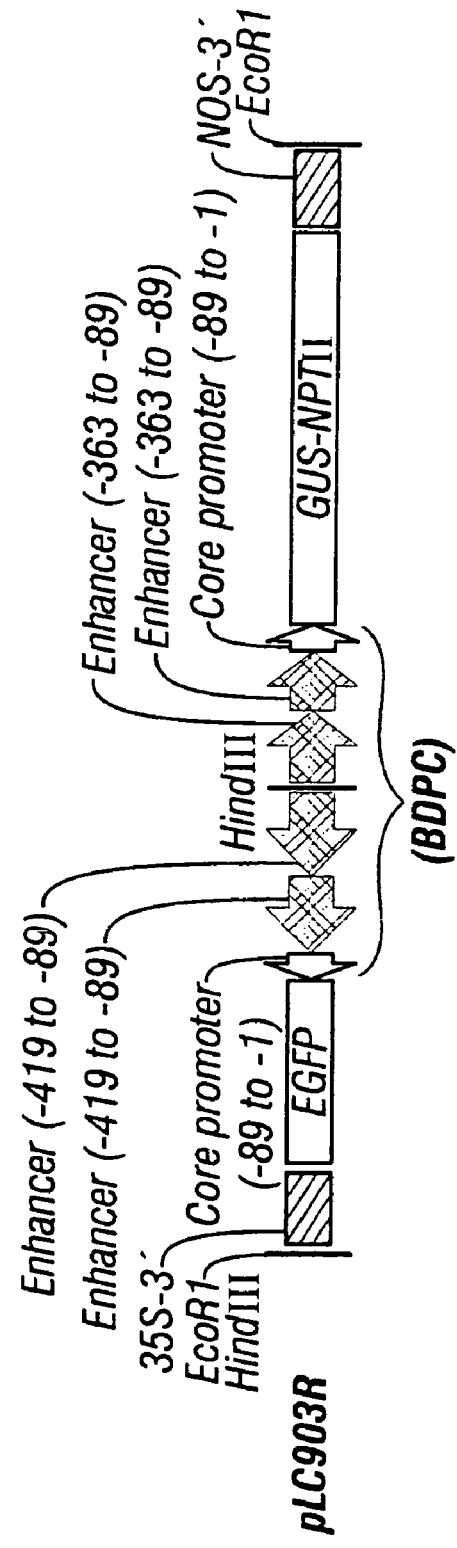

To investigate transgene expression directed by a BDPC containing 4 enhancers, two transformation vectors pLC903T and pLC903R were constructed. As shown in FIG. 26, both vectors contained an EGFP expression unit and a GUS-containing expression unit. The two expression units were under the control of a similar enhanced double CaMV 35S promoter with a slightly different sequence length of enhancers. In pLC903T the two expression units were placed in a tandem orientation. The two expression units in pLC903R were placed in a divergent (back-to-back) orientation, thus resulting in the formation of a 4-enhancer-containing BDPC for the expression of both EGFP and GUS genes. The BDPC configuration in pLC903R is basically similar to that as illustrated in FIG. 3.

Figure 27:
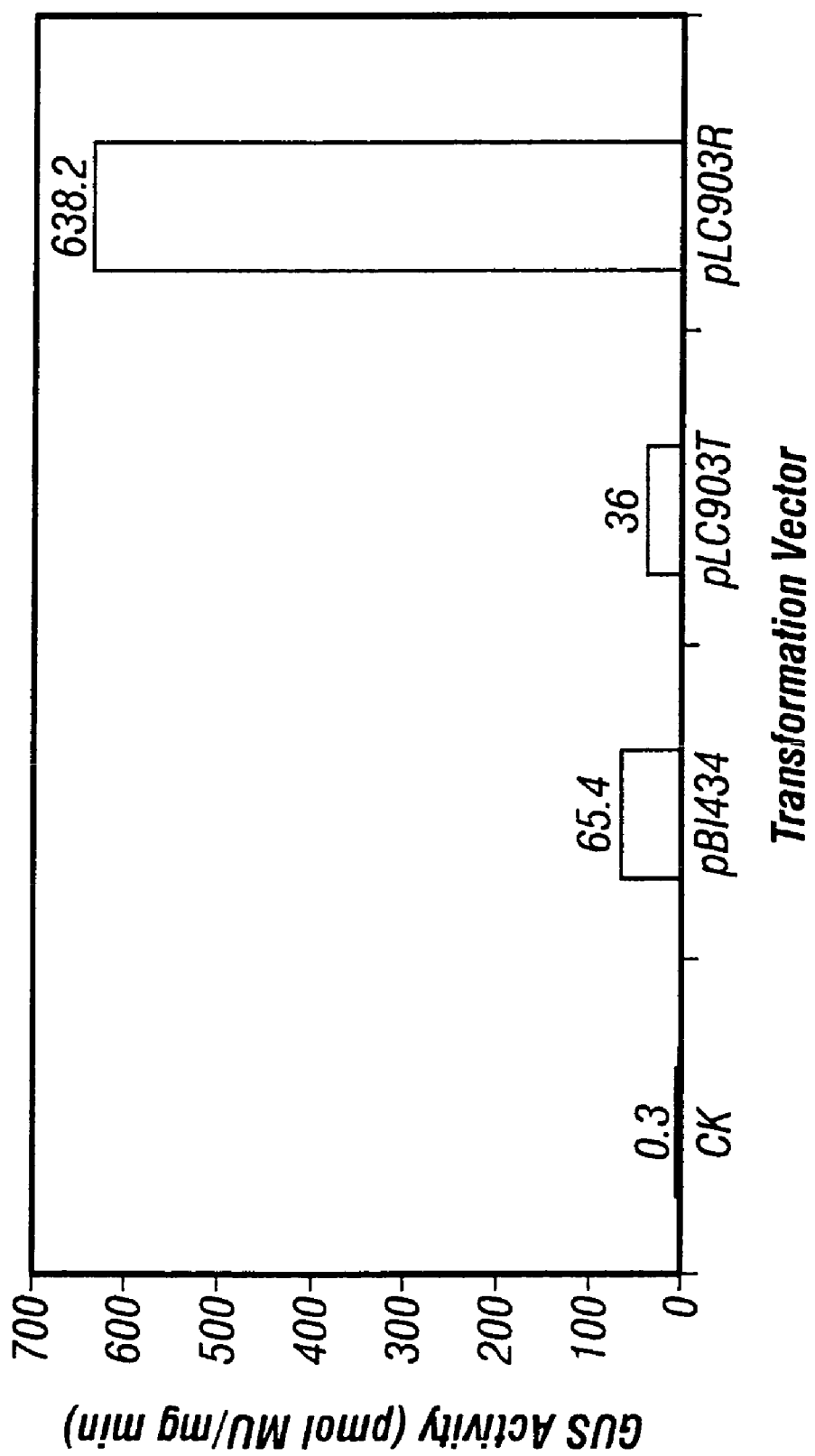
FIG. 27 shows the analysis of GUS activity in SE (*V. Vinifera* cv. Thompson Seedless) lines after transformation using three binary vectors.

Both pLC903T and pLC903R were introduced into *A. tumefaciens* and subsequently used in transformation of grape SE along with a control transformation vector pBI434 as previously described in Examples 2 and 3. The level of GUS expression in transformed SE was determined subsequently and the averaged results from three independent experiments were summarized in FIG. 27. In these experiments, GUS activity obtained from 30-min reactions was used for data conversion. Results indicated that there was no GUS-specific activity in non-transformed SE (CK-0.3 pmol MU/mg/min). Surprisingly, the GUS activity obtained from SE transformed with pLC903T was about half of that observed from pLC434 (36 vs. 65.4 pmol MU/mg/min), even though the GUS expression unit in both vectors was identical and was controlled by the same enhanced double CaMV 35S promoter. The reduction in GUS expression observed from the use of pLC903T could be accounted for by the possible interference of terminator sequences (35S-31) in the upstream region of the GUS expression unit in pLC903T. On the contrary, an increase in GUS activity by almost 10-fold was observed in SE transformed with pLC903R, which contains a 4-enhancer-containing BDPC in the upstream region of the core promoter, as compared to the GUS activity from pBI434, which only contained an enhanced double CaMV35S promoter (638.2 vs. 65.4 pmol MU/mg/min). The dramatic increase in GUS expression by using transformation vector pLC903R further demonstrated the significant enhancement of trangene expression from the use of unique BDPC promoter configuration as elucidated in this invention.

Numerous modifications and variations in practice of the invention are expected to occur to those skilled in the art upon consideration of the foregoing detailed ;description of the invention. Consequently, such modifications and variations are intended to be included within the scope of the following claims.

What is claimed is:

1. A bidirectional promoter complex comprising:
   a modified enhancer region that includes two enhancer sequences; and
   two core promoters, the core promoters being on either side of the modified enhancer region in a divergent orientation; wherein the bidirectional promoter complex includes SEQ ID NO:1.

2. The bidirectional promoter complex of claim 1 wherein the modified enhancer includes two tandem oriented enhancer sequence having substantial sequence identity.

3. The bidirectional promoter complex of claim 1 wherein the modified enhancer region is constructed such that a 3' end of a first enhancer sequence is linked to a 5' end of a second enhancer sequence.

4. The bidirectional promoter complex of claim 1 wherein the core promoters are fused to either end of the modified enhancer region in a divergent orientation.

5. The bidirectional promoter complex of claim 1 wherein each core promoter includes a TATA-box concensus element and an Initiator.

6. The bidirectional promoter complex of claim 5 wherein each core promoter further includes at least one cis-acting element.

7. A vector comprising a biderectional promoter complex, the biderectional promotr complex including a modified enhancer region and two core promoter, the core promoters being on either side of the modified enhancer complex in a divergent orientation; wherein the biderectional promoter complex includes SEQ ID NO:1.

8. An eukaryotic cell transfected with a vector, the vector comprising a bidirectional promoter complex, the bidirectional promoter complex including a modified enhancer region and two core promoters, the core promoters being on either side of the modified enhancer complex in a divergent orientation; wherein the bidirectional promoter complex includes SEQ ID NO:1.

9. A method for improving transcription efficiency of transgenes, the method comprising inserting the transgene into a vector, such that the transgene is operably linked to a bidirectional promoter complex, the bidirectional promoter complex including a modified enhancer region and two core promoters, the core promoters being on either side of the modified enhancer complex in a divergent orientation, wherein the bidirectional promoter complex includes SEQ ID NO:1, and wherein said bidirectional promoter complex improves transcription efficiency of said transgene.

10. A method for producing one or more polypeptides encoded by a transgene, the method comprising inserting said transgene into a vector, wherein the transgene is operably linked to a bidirectional promoter complex, the bidirectional promoter complex including a modified enhancer region and two core promoters, the core promoters being on either side of the modified enhancer complex in a divergent orientation, wherein the bidirectional promoter complex includes SEQ ID NO:1; introducing said vector into a host cell; culturing said host cell under appropriate condition so that one or more polypeptide encoded by the transgene is produced.

* * * * *

UNITED STATES PATENT AND TRADEMARK OFFICE
CERTIFICATE OF CORRECTION

PATENT NO. : 7,129,343 B2 Page 1 of 1
APPLICATION NO. : 10/075105
DATED : October 31, 2006
INVENTOR(S) : Li et al.

It is certified that error appears in the above-identified patent and that said Letters Patent is hereby corrected as shown below:

Title page, item (75) Iventors: delete "Apopka" and insert --Altamonte Springs--, therefor.

Title page, item (75) Inventors: delete "Howy in the Hills" and insert --Howey in the Hills--, therefor.

Column 43, Line 26: delete "biderectional promotr" and inset --bidirectional promoter--, therefor.

Column 43, line 27: delete "promoter" and insert --promoters--, therefor.

Column 43, line 29: delete "biderectional" and insert --bidirectional--, therefor.

Column 44, Line 25: delete "biderectional" and insert --bidirectional--, therefor.

Signed and Sealed this

Sixteenth Day of January, 2007

JON W. DUDAS
*Director of the United States Patent and Trademark Office*

SEQUENCE LISTING

<160> NUMBER OF SEQ ID NOS: 18

<210> SEQ ID NO 1
<211> LENGTH: 736
<212> TYPE: DNA
<213> ORGANISM: CaMV 35S
<220> FEATURE:
<223> OTHER INFORMATION:

<400> SEQUENCE: 1

```
ggatccagcg tgtcctctcc aaatgaaatg aacttcctta tatagaggaa gggtcttgcg      60
aaggatagtg ggattgtgcg tcatcccta cgtcagtgga gatactgcag aagcttctgc     120
agtgagactt ttcaacaaag ggtaatatcg ggaaacctcc tcggattcca ttgcccagct    180
atctgtcact tcatcaaaag gacagtagaa aaggaaggtg gcacctacaa atgccatcat    240
tgcgataaag gaaaggctat cgttcaagat gcctctgccg acagtggtcc caaagatgga    300 ccccccaccca cgaggagcat cgtggaaaaa gaagacgttc caaccacgtc ttcaaagcaa    360
gtggattgat gtgattgcag tgagactttt caacaaaggg taatatcggg aaacctcctc    420
ggattccatt gcccagctat ctgtcacttc atcaaaagga cagtagaaaa ggaaggtggc    480
acctacaaat gccatcattg cgataaagga aaggctatcg ttcaagatgc ctctgccgac    540
agtggtccca aagatggacc cccacccacg aggagcatcg tggaaaaaga agacgttcca    600
accacgtctt caaagcaagt ggattgatgt gatatctcca ctgacgtaag ggatgacgca    660
caatcccact atccttcgca agacccttcc tctatataag gaagttcatt tcatttggag    720
aggacacgct ggatcc                                                    736
```

<210> SEQ ID NO 2
<211> LENGTH: 736
<212> TYPE: DNA
<213> ORGANISM: CaMV 35S
<220> FEATURE:
<223> OTHER INFORMATION:

<400> SEQUENCE: 2

```
cctaggtcgc acaggagagg tttactttac ttgaaggaat atatctcctt cccagaacgc      60
ttcctatcac cctaacacgc agtagggaat gcagtcacct ctatgacgtc ttcgaagacg    120
tcactctgaa aagttgtttc ccattatagc cctttggagg agcctaaggt aacgggtcga    180
tagacagtga agtagttttc ctgtcatctt ttccttccac cgtggatgtt tacggtagta    240
acgctatttc ctttccgata gcaagttcta cggagacggc tgtcaccagg gtttctacct    300
gggggtgggt gctcctcgta gcaccttttt cttctgcaag gttggtgcag aagtttcgtt    360
cacctaacta cactaacgtc actctgaaaa gttgtttccc attatagccc tttggaggag    420
cctaaggtaa cgggtcgata gacagtgaag tagttttcct gtcatctttt ccttccaccg    480
```

```
tggatgttta cggtagtaac gctatttcct ttccgatagc aagttctacg gagacggctg      540
tcaccagggt ttctacctgg gggtgggtgc tcctcgtagc accttttct tctgcaaggt       600 tggtgcagaa gtttcgttca cctaactaca ctatagaggt gactgcattc cctactgcgt      660
gttagggtga taggaagcgt tctgggaagg agatatattc cttcaagtaa agtaaacctc      720
tcctgtgcga cctagg                                                      736
```

<210> SEQ ID NO 3
<211> LENGTH: 1360
<212> TYPE: DNA
<213> ORGANISM: CaMV 35S
<220> FEATURE:
<223> OTHER INFORMATION:

<400> SEQUENCE: 3

```
tacgtacagc gtgtcctctc caaatgaaat gaacttcctt atatagagga agggtcttgc       60
gaaggatagt gggattgtgc gtcatccctt acgtcagtgg agatatcaca tccatccact      120
tgctttgaag acgtggttgg aacgtcttct ttttccacga tgctcctcgt gggtgggggt      180
ccatctttgg gaccactgtc ggcagaggca tcttcaacga tggcctttcc tttatcgcaa      240
tgatggcatt tgtaggagcc accttccttt tccactatct tcacaataaa gtgacagata      300
gctgggcaat ggaatccgag gaggtttccg gatattaccc tttgttgaaa agtctcaatt      360
gccctttggt cttctgagac tgtatctttg atatttttgg agtagacaag tgtgtcgtgc      420
tccaccatgt tgattcacat caatccactt gctttgaaga cgtggttgga acgtcttctt      480
tttccacgat gctcctcgtg ggtgggggtc catctttggg accactgtcg gcagaggcat      540
cttcaacgat ggcctttcct ttatcgcaat gatggcattt gtaggagcca ccttcctttt      600
ccactatctt cacaataaag tgacagatag ctgggcaatg gaatccgagg aggtttccgg      660
atattaccct ttgttgaaaa gtctcaattg ccctttggtc ttctgagact gtatctttga      720 tattttttgga gtagacaagt gtgtcgtgct ccaccatgtt gataagcttc tgcagtgaga      780
cttttcaaca aagggtaata tcgggaaacc tcctcggatt ccattgccca gctatctgtc      840
acttcatcaa aggacagta gaaaggaag gtggcaccta caaatgccat cattgcgata       900
aaggaaaggc tatcgttcaa gatgcctctg ccgacagtgg tcccaaagat ggaccccccac     960 ccacgaggag catcgtggaa aaagaagacg ttccaaccac gtcttcaaag caagtggatt     1020
gatgtgattg cagtgagact tttcaacaaa gggtaatatc gggaaacctc ctcggattcc     1080
attgcccagc tatctgtcac ttcatcaaaa ggacagtaga aaaggaaggt ggcacctaca     1140
aatgccatca ttgcgataaa ggaaaggcta tcgttcaaga tgcctctgcc gacagtggtc     1200
ccaaagatgg acccccaccc acgaggagca tcgtggaaaa agaagacgtt ccaaccacgt     1260
cttcaaagca gtggattga tgtgatatct ccactgacgt aagggatgac gcacaatccc     1320
actatccttc gcaagaccct tcctctatat aaggaagttc                           1360
```

<210> SEQ ID NO 4
<211> LENGTH: 1360
<212> TYPE: DNA
<213> ORGANISM: CaMV 35S
<220> FEATURE:
<223> OTHER INFORMATION:

<400> SEQUENCE: 4

```
atgcatgtcg cacaggagag gtttactttta cttgaaggaa tatatctcct tcccagaacg       60
```

-continued

| | |
|---|---|
| cttcctatca ccctaacacg cagtagggaa tgcagtcacc tctatagtgt agttaggtga | 120 |
| acgaaacttc tgcaccaacc ttgcagaaga aaaggtgct acgaggagca cccaccccca | 180 |
| ggtagaaacc ctggtgacag ccgtctccgt agaagttgct accggaaagg aaatagcgtt | 240 |
| actaccgtaa acatcctcgg tggaaggaaa aggtgataga agtgttattt cactgtctat | 300 |
| cgacccgtta ccttaggctc ctccaaaggc ctataatggg aaacaacttt tcagagttaa | 360 |
| cgggaaacca gaagactctg acatagaaac tataaaaacc tcatctgttc acacagcacg | 420 |
| aggtggtaca actaagtgta gttaggtgaa cgaaacttct gcaccaacct tgcagaagaa | 480 |
| aaaggtgcta cgaggagcac ccaccccag gtagaaaccc tggtgacagc cgtctccgta | 540 |
| gaagttgcta ccggaaagga aatagcgtta ctaccgtaaa catcctcggt ggaaggaaaa | 600 |
| ggtgatagaa gtgttatttc actgtctatc gacccgttac cttaggctcc tccaaaggcc | 660 |
| tataatggga acaacttttt cagagttaac gggaaaccag aagactctga catagaaact | 720 |
| ataaaaacct catctgttca cacagcacga ggtggtacaa ctattcgaag acgtcactct | 780 |
| gaaaagttgt ttcccattat agccctttgg aggagcctaa ggtaacgggt cgatagacag | 840 |
| tgaagtagtt ttcctgtcat cttttccttc caccgtggat gtttacggta gtaacgctat | 900 |
| ttcctttccg atagcaagtt ctacggagac ggctgtcacc agggtttcta cctggggggtg | 960 |
| ggtgctcctc gtagcacctt tttcttctgc aaggttggtg cagaagtttc gttcacctaa | 1020 |
| ctacactaac gtcactctga aaagttgttt cccattatag ccctttggag gagcctaagg | 1080 |
| taacgggtcg atagacagtg aagtagtttt cctgtcatct tttccttcca ccgtggatgt | 1140 |
| ttacggtagt aacgctattt cctttccgat agcaagttct acggagacgg ctgtcaccag | 1200 |
| ggtttctacc tggggggtggg tgctcctcgt agcaccttt tcttctgcaa ggttggtgca | 1260 |
| gaagtttcgt tcacctaact acactataga ggtgactgca ttccctactg cgtgttaggg | 1320 |
| tgataggaag cgttctggga aggagatata ttccttcaag | 1360 |

<210> SEQ ID NO 5
<211> LENGTH: 1052
<212> TYPE: DNA
<213> ORGANISM: CaMV 35S
<220> FEATURE:
<223> OTHER INFORMATION:

<400> SEQUENCE: 5

| | |
|---|---|
| ggatccacaa acttacaaat ttctctgaag ttgtatcctc agtacttcaa agaaaatagc | 60 |
| ttacaccaaa ttttttcttg ttttcacaaa tgccgaactt ggttccttat ataggaaaac | 120 |
| tcaagggcaa aaatgacacg gaaaaatata aaggataag tagtgggggga taagattcct | 180 |
| ttgtgataag gttactttcc gaagcttcca gaaggtaatt atccaagatg tagcatcaag | 240 |
| aatccaatgt ttacgggaaa aactatggaa gtattatgtg agctcagcaa gaagcagatc | 300 |
| aatatgcggc acatatgcaa cctatgttca aaatgaagaa atgtacagat acaagatcct | 360 |
| atactgccag aatacgaaga gaatacgta gaaattgaaa agaagaacc aggcgaagaa | 420 |
| aagaatcttg aagacgtaag cactgacgac aacaatgaaa agaagaagat aaggtcggtg | 480 |
| attgtgaaag agacatagag gacacatgta aggtggaaaa tgtaagggct gcagaaggta | 540 |
| attatccaag atgtagcatc aagaatccaa tgtttacggg aaaaactatg gaagtattat | 600 |
| gtgagctcag caagaagcag atcaatatgc ggcacatatg caacctatgt tcaaaaatga | 660 |
| agaatgtaca gatacaagat cctatactgc cagaatacga agaagaatac gtagaaattg | 720 |
| aaaaagaaga accaggcgaa gaaaagaatc ttgaagacgt aagcactgac gacaacaatg | 780 |

| | |
|---|---|
| aaaagaagaa gataaggtcg gtgattgtga aagagacata gaggacacat gtaaggtgga | 840 |
| aaatgtaagg gcggaaagta accttatcac aaaggaatct tatcccccac tacttatcct | 900 |
| tttatatttt tccgtgtcat ttttgccctt gagttttcct atataaggaa ccaagttcgg | 960 |
| catttgtgaa acaagaaaa aatttggtgt aagctatttt ctttgaagta ctgaggatac | 1020 |
| aacttcagag aaatttgtaa gtttgtggat cc | 1052 |

<210> SEQ ID NO 6
<211> LENGTH: 1052
<212> TYPE: DNA
<213> ORGANISM: CaMV 35S
<220> FEATURE:
<223> OTHER INFORMATION:

<400> SEQUENCE: 6

| | |
|---|---|
| cctaggtgtt tgaatgttta aagagacttc aacataggag tcatgaagtt tcttttatcg | 60 |
| aatgtggttt aaaaaagaac aaaagtgttt acggcttgaa ccaaggaata tatccttttg | 120 |
| agttcccgtt tttactgtgc ctttttatat tttcctattc atcaccccct attctaagga | 180 |
| aacactattc caatgaaagg cttcgaaggt cttccattaa taggttctac atcgtagttc | 240 |
| ttaggttaca aatgcccttt ttgataccct cataatacac tcgagtcgtt cttcgtctag | 300 |
| ttatacgccg tgtatacgtt ggatacaagt ttttacttct tacatgtcta tgttctagga | 360 |
| tatgacggtc ttatgcttct tcttatgcat ctttaacttt tcttcttgg tccgcttctt | 420 |
| ttcttagaac ttctgcattc gtgactgctg ttgttacttt tcttcttcta ttccagccac | 480 |
| taacactttc tctgtatctc ctgtgtacat tccacctttt acattcccga cgtcttccat | 540 |
| taataggttc tacatcgtag ttcttaggtt acaaatgccc ttttgatac cttcataata | 600 |
| cactcgagtc gttcttcgtc tagttatacg ccgtgtatac gttggataca agttttact | 660 |
| tcttacatgt ctatgttcta ggatatgacg gtcttatgct tcttcttatg catctttaac | 720 |
| tttttcttct tggtccgctt cttttcttag aacttctgca ttcgtgactg ctgttgttac | 780 |
| ttttcttctt ctattccagc cactaacact ttctctgtat ctcctgtgta cattccacct | 840 |
| tttacattcc cgcctttcat tggaatagtg tttccttaga ataggggtg atgaatagga | 900 |
| aaatataaaa aggcacagta aaaacgggaa ctcaaaagga tatattcctt ggttcaagcc | 960 |
| gtaaacactt tgttcttttt taaaccaca ttcgataaaa gaaacttcat gactcctatg | 1020 |
| ttgaagtctc tttaaacatt caaacaccta gg | 1052 |

<210> SEQ ID NO 7
<211> LENGTH: 1590
<212> TYPE: DNA
<213> ORGANISM: CaMV 35S
<220> FEATURE:
<223> OTHER INFORMATION:

<400> SEQUENCE: 7

| | |
|---|---|
| ggatccacaa acttacaaat ttctctgaag ttgtatcctc agtacttcaa agaaaatagc | 60 |
| ttacaccaaa tttttttcttg ttttcacaaa tgccgaactt ggttccttat ataggaaaac | 120 |
| tcaagggcaa aaatgacacg gaaaaatata aaaggataag tagtgggga taagattcct | 180 |
| ttgtgataag gttactttcc gcccttacat tttccacctt acatgtgtcc tctatgtctc | 240 |
| tttcacaatc accgaccta tcttcttctt tcattgttg tcgtcagtgc ttacgtcttc | 300 |
| aagattcttt tcttcgcctg gttcttcttt ttcaatttct acgtattctt cttcgtattc | 360 |

-continued

```
tggcagtata ggatcttgta tctgtacatt cttcattttt gaacataggt tgcatatgtg    420
ccgcatattg atctgcttct tgctgagctc acataatact tccatagctg cagcccttac    480
attttccacc ttacatgtgt cctctatgtc tctttcacaa tcaccgacct tatcttcttc    540
ttttcattgt tgtcgtcagt gcttacgtct tcaagattct tttcttcgcc tggttcttct    600
ttttcaattt ctacgtattc ttcttcgtat tctggcagta taggatcttg tatctgtaca    660
ttcttcattt ttgaacatag gttgcatatg tgccgcatat tgatctgctt cttgctgagc    720
tcacataata cttccatagg aagcttcaga aggtaattat ccaagatgta gcatcaagaa    780
tccaatgttt acgggaaaaa ctatggaagt attatgtgag ctcagcaaga agcagatcaa    840
tatgcggcac atatgcaacc tatgttcaaa atgaagaat gtacagatac aagatcctat     900
actgccagaa tacgaagaag aatacgtaga aattgaaaaa gaagaaccag gcgaagaaaa    960
gaatcttgaa gacgtaagca ctgacgacaa caatgaaaag aagaagataa ggtcggtgat   1020
tgtgaaagag acatagagga cacatgtaag gtggaaaatg taagggctgc agaaggtaat   1080
tatccaagat gtagcatcaa gaatccaatg tttacgggaa aaactatgga agtattatgt   1140
gagctcagca agaagcagat caatatgcgg cacatatgca acctatgttc aaaaatgaag   1200
aatgtacaga tacaagatcc tatactgcca gaatacgaag aagaatacgt agaaattgaa   1260
aaagaagaac aggcgaagaa aaagaatctt gaagacgtaa gcactgacga caacaatgaa   1320
aagaagaaga taaggtcggt gattgtgaaa gagacataga ggacacatgt aaggtggaaa   1380
atgtaagggc ggaaagtaac cttatcacaa aggaatctta tcccccacta cttatccttt   1440 tatattttc cgtgtcattt tgcccttga gttttcctat ataaggaacc aagttcggca    1500
tttgtgaaaa caagaaaaaa tttggtgtaa gctattttct ttgaagtact gaggatacaa   1560
cttcagagaa atttgtaagt tgtggatcc                                     1590
```

<210> SEQ ID NO 8
<211> LENGTH: 1590
<212> TYPE: DNA
<213> ORGANISM: CaMV 35S
<220> FEATURE:
<223> OTHER INFORMATION:

<400> SEQUENCE: 8

```
cctaggtgtt tgaatgttta aagagacttc aacataggag tcatgaagtt tcttttatcg     60
aatgtggttt aaaaaagaac aaaagtgttt acggcttgaa ccaaggaata tatccttttg    120
agttcccgtt tttactgtgc cttttttatat tttcctattc atcacccct attctaagga    180 aacactattc caatgaaagg cggggatgta aaggtggaa tgtacacagg agatacagag    240
aaagtgttag tggctggaat agaagaagaa agtaacaac agcagtcacg aatgcagaag    300
ttctaagaaa agaagcggac caagaagaaa agttaaaga tgcataagaa gaagcataag    360
accgtcatat cctagaacat agacatgtaa gaagtaaaaa cttgtatcca acgtatacac    420
ggcgtataac tagacgaaga acgactcgag tgtattatga aggtatcgac gtcgggaatg    480 taaaggtgg aatgtacaca ggagatacag agaaagtgtt agtggctgga atagaagaag    540 aaagtaaca acagcagtca cgaatgcaga agttctaaga aagaagcgg accaagaaga    600 aaaagttaaa gatgcataag aagaagcata agaccgtcat atcctagaac atagacatgt    660
aagaagtaaa acttgtatc caacgtatac acggcgtata actagacgaa gaacgactcg    720
agtgtattat gaaggtatcc ttcgaagtct tccattaata ggttctacat cgtagttctt    780
aggttacaaa tgcccttttt gataccttca taatacactc gagtcgttct tcgtctagtt    840
```

-continued

```
atacgccgtg tatacgttgg atacaagttt ttacttctta catgtctatg ttctaggata      900
tgacggtctt atgcttcttc ttatgcatct ttaactttt cttcttggtc cgcttctttt       960 cttagaaactt ctgcattcgt gactgctgtt gttacttttc ttcttctatt ccagccacta    1020
acactttctc tgtatctcct gtgtacattc cacctttac attcccgacg tcttccatta     1080
ataggttcta catcgtagtt cttaggttac aaatgccctt tttgataccct tcataataca   1140 ctcgagtcgt tcttcgtcta gttatacgcc gtgtatacgt tggatacaag ttttacttc     1200 ttacatgtct atgttctagg atatgacggt cttatgcttc ttcttatgca tctttaactt    1260
tttcttcttg gtccgcttct tttcttagaa cttctgcatt cgtgactgct gttgttactt    1320
ttcttcttct attccagcca ctaacacttt ctctgtatct cctgtgtaca ttccaccttt    1380
tacattcccg cctttcattg aatagtgtt tccttagaat aggggtgat gaataggaaa      1440 atataaaaag gcacagtaaa aacgggaact caaaaggata tattccttgg ttcaagccgt   1500
aaacactttt gttctttttt aaaccacatt cgataaaaga aacttcatga ctcctatgtt    1560
gaagtctctt taaacattca aacacctagg                                     1590
```

<210> SEQ ID NO 9
<211> LENGTH: 1228
<212> TYPE: DNA
<213> ORGANISM: ACT2
<220> FEATURE:
<223> OTHER INFORMATION:

<400> SEQUENCE: 9

```
ggatccttgt tttcaaagcg gagaggaaaa tatatgaatt tatataggcg ggtttatctc     60
ttacaacttt attttcggcc tttcaaaaaa ataattaaaa tcgacagaca cgaatcattt    120
cgaccacaga agcttcaact atttttatgt atgcaagagt cagcatatgt ataattgatt    180
cagaatcgtt ttgacgagtt cggatgtagt agtagccatt atttaatgta catactaatc   240
gtgaatagtg atatgatgaa acattgtatc ttattgtata aatatccata aacacatcat   300
gaaagacact ttcttttcacg gtctgaatta attatgatac aattctaata gaaaacgaat  360
taaattacgt tgaattgtat gaaatctaat tgaacaagcc aaccacgacg acgactaacg   420
ttgcctggat tgactcggtt taagttaacc actaaaaaaa cggagctgtc atgtaacacg    480
cggatcgagc aggtcacagt catgaagcca tcaaagcaaa agaactaatc caagggctga   540
gatgattaat tagtttaaaa attagttaac acgagggaaa aggctgtctg acagccaggt    600
cacgttatct ttacctgcag caactatttt tatgtatgca agagtcagca tatgtataat   660
tgattcagaa tcgttttgac gagttcggat gtagtagtag ccattatttta atgtacatac  720 taatcgtgaa tagtgatatg atgaaacatt gtatcttatt gtataaatat ccataaacac   780
atcatgaaag acactttctt tcacggtctg aattaattat gatacaattc taatagaaaa   840
cgaattaaat tacgttgaat tgtatgaaat ctaattgaac aagccaacca cgacgacgac   900
taacgttgcc tggattgact cggtttaagt taaccactaa aaaacggag ctgtcatgta     960 acacgcggat cgagcaggtc acagtcatga agccatcaaa gcaaagaaac taatccaagg   1020
gctgagatga ttaattagtt taaaaattag ttaacacgag ggaaaaggct gtctgacagc   1080
caggtcacgt tatctttacc tgtggtcgaa atgattcgtg tctgtcgatt ttaattattt   1140
ttttgaaagg ccgaaaataa agttgtaaga gataaacccg cctatataaa ttcatatatt   1200
ttcctctccg ctttgaaaac aaggatcc                                      1228
```

<210> SEQ ID NO 10
<211> LENGTH: 1228
<212> TYPE: DNA
<213> ORGANISM: ACT2
<220> FEATURE:
<223> OTHER INFORMATION:

<400> SEQUENCE: 10

| | | | | | |
|---|---|---|---|---|---|
| cctaggaaca | aaagtttcgc | ctctcctttt | atatacttaa | atatatccgc | ccaaatagag | 60 |
| aatgttgaaa | taaagccgg | aaagttttt | tattaatttt | agctgtctgt | gcttagtaaa | 120 |
| gctggtgtct | tcgaagttga | taaaaataca | tacgttctca | gtcgtataca | tattaactaa | 180 |
| gtcttagcaa | aactgctcaa | gcctacatca | tcatcggtaa | taaattacat | gtatgattag | 240 |
| cacttatcac | tatactactt | tgtaacatag | aataacatat | ttataggtat | ttgtgtagta | 300 |
| ctttctgtga | agaaagtgc | cagacttaat | taatactatg | ttaagattat | cttttgctta | 360 |
| atttaatgca | acttaacata | ctttagatta | acttgttcgg | ttggtgctgc | tgctgattgc | 420 |
| aacggaccta | actgagccaa | attcaattgg | tgatttttt | gcctcgacag | tacattgtgc | 480 |
| gcctagctcg | tccagtgtca | gtacttcggt | agtttcgttt | tcttgattag | gttcccgact | 540 |
| ctactaatta | atcaaatttt | taatcaattg | tgctcccttt | tccgacagac | tgtcggtcca | 600 |
| gtgcaataga | aatggacgtc | gttgataaaa | atacatacgt | tctcagtcgt | atacatatta | 660 |
| actaagtctt | agcaaaactg | ctcaagccta | catcatcatc | ggtaataaat | tacatgtatg | 720 |
| attagcactt | atcactatac | tactttgtaa | catagaataa | catatttata | ggtatttgtg | 780 |
| tagtactttc | tgtgaaagaa | agtgccagac | ttaattaata | ctatgttaag | attatctttt | 840 |
| gcttaattta | atgcaactta | acatactttta | gattaacttg | ttcggttggt | gctgctgctg | 900 |
| attgcaacgg | acctaactga | gccaaattca | attggtgatt | ttttgcctc | gacagtacat | 960 |
| tgtgcgccta | gctcgtccag | tgtcagtact | tcggtagttt | cgttttcttg | attaggttcc | 1020 |
| cgactctact | aattaatcaa | atttttaatc | aattgtgctc | ccttttccga | cagactgtcg | 1080 |
| gtccagtgca | atagaaatgg | acaccagctt | tactaagcac | agacagctaa | aattaataaa | 1140 |
| aaaactttcc | ggcttttatt | tcaacattct | ctatttgggc | ggatatattt | aagtatataa | 1200 |
| aaggagaggc | gaaacttttg | ttcctagg | | | | 1228 |

<210> SEQ ID NO 11
<211> LENGTH: 1544
<212> TYPE: DNA
<213> ORGANISM: ACT2
<220> FEATURE:
<223> OTHER INFORMATION:

<400> SEQUENCE: 11

| | | | | | |
|---|---|---|---|---|---|
| ggatcctttt | gggttttggt | gagaaacaag | gaatagtatg | gatgggtttt | aatagggaat | 60 |
| aagagttgaa | aagtctgcaa | tttgtaaaag | aaaaaaattg | gaaagtcaca | tgttagcaga | 120 |
| agcttcagac | tcattaactt | aaaagaagat | atagactcat | taacttaaaa | gaagatatag | 180 |
| attccaacac | aagttcaaaa | ttcataaacg | tcaatcttgg | ctaaatttct | gaacatcaat | 240 |
| gcattccttt | aaaatataga | taataagtta | ggatgttgtc | actttcttaa | agcatattcc | 300 |
| gactgagtct | ggtagaatct | cataaacttt | aggccttatc | tcttcaatta | ggcaattact | 360 |
| tacctccgct | ctacttttaag | aaaattcaat | ggagtacacc | attattaagt | tcatataaaa | 420 |
| ataaaattat | attaattctg | tctccttgttg | gttcgctcta | tcttttttctg | ttttcctgct | 480 |
| tcaaccataa | catatacaag | aactacattt | tccaagctag | atatatctaa | catgactgac | 540 |

-continued

```
tttgtaaatt tcttttgcca agttaaagaa aaaaaatgat gttatccaaa taataaagag    600
aaagagccct aatgaaaaaa atgatttact attagagttg ttcagctaat cacatcaatt    660
atggttttca tcaagtatga ctaatggcgg ctcttatctc agctgatgtg acattgaaat    720
tctttgactt taacactaat gtcatatgct ttcaaattaa taatccgata aagctgcaga    780
ctcattaact taaagaaga tatagactca ttaacttaaa agaagatata gattccaaca    840
caagttcaaa attcataaac gtcaatcttg ctaaatttc tgaacatcaa tgcattcctt    900
taaaatatag ataataagtt aggatgttgt cactttctta aagcatattc cgactgagtc    960
tggtagaatc tcataaactt taggccttat ctcttcaatt aggcaattac ttacctccgc   1020
tctactttaa gaaattcaa tggagtacac cattattaag ttcatataaa aataaaatta   1080
tattaattct gtctcttgtt ggttcgctct atctttttct gttttcctgc ttcaaccata   1140
acatatacaa gaactacatt ttccaagcta gatatatcta acatgactga ctttgtaaat   1200
ttcttttgcc aagttaaaga aaaaaatga tgttatccaa ataataaaga gaaagagccc   1260
taatgaaaaa aatgatttac tattagagtt gttcagctaa tcacatcaat tatggttttc   1320
atcaagtatg actaatggcg gctcttatct cacgtgatgt gacattgaaa ttctttgact   1380
ttaacactaa tgtcatatgc tttcaaatta ataatccgat aaagtctgct aacatgtgac   1440
tttccaattt ttttctttta caaattgcag acttttcaac tcttattccc tattaaaacc   1500
catccatact attccttgtt tctcaccaaa acccaaaagg atcc                    1544
```

<210> SEQ ID NO 12
<211> LENGTH: 1544
<212> TYPE: DNA
<213> ORGANISM: ACT2
<220> FEATURE:
<223> OTHER INFORMATION:

<400> SEQUENCE: 12

```
cctaggaaaa cccaaaacca ctctttgttc cttatcatac ctacccaaaa ttatcccatt     60
ttctcaactt ttcagacgtt aaacatttc tttttttaac ctttcagtgt acaatcgtct    120
tcgaagtctg agtaattgaa ttttcttcta tatctgagta attgaatttt cttctatatc    180
taaggttgtg ttcaagtttt aagtatttgc agttagaacc gatttaaaga cttgtagtta    240
cgtaaggaaa ttttatatct attattcaat cctacaacag tgaaagaatt tcgtataagg    300
ctgactcaga ccatcttaga gtatttgaaa tccggaatag agaagttaat ccgttaatga    360
atggaggcga gatgaaattc ttttaagtta cctcatgtgg taataattca agtatatttt    420
tatttttaata taattaagac agagaacaac caagcgagat agaaaaagac aaaaggacga    480
agttggtatt gtatatgttc ttgatgtaaa aggttcgatc tatatagatt gtactgactg    540
aaacatttaa agaaacggt tcaatttctt ttttttacta caataggttt attatttctc    600
tttctcggga ttacttttt tactaaatga taatctcaac aagtcgatta gtgtagttaa    660
taccaaaagt agttcatact gattaccgcc gagaatagag tgcactacac tgtaacttta    720
agaaactgaa attgtgatta cagtatacga aagtttaatt attaggctat ttcgacgtct    780
gagtaattga attttcttct atatctgagt aattgaattt tcttctatat ctaaggttgt    840
gttcaagttt taagtatttg cagttagaac cgatttaaag acttgtagtt acgtaaggaa    900
attttatatc tattattcaa tcctacaaca gtgaaagaat tcgtataag gctgactcag    960
accatcttag agtatttgaa atccggaata gagaagttaa tccgttaatg aatggaggcg   1020
```

-continued

| | |
|---|---|
| agatgaaatt cttttaagtt acctcatgtg gtaataattc aagtatattt ttattttaat | 1080 |
| ataattaaga cagagaacaa ccaagcgaga tagaaaaaga caaaaggacg aagttggtat | 1140 |
| tgtatatgtt cttgatgtaa aaggttcgat ctatatagat tgtactgact gaaacattta | 1200 |
| aagaaaacgg ttcaatttct ttttttttact acaataggtt tattatttct ctttctcggg | 1260 |
| attacttttt ttactaaatg ataatctcaa caagtcgatt agtgtagtta ataccaaaag | 1320 |
| tagttcatac tgattaccgc cgagaataga gtgcactaca ctgtaacttt aagaaactga | 1380 |
| aattgtgatt acagtatacg aaagtttaat tattaggcta tttcagacga ttgtacactg | 1440 |
| aaaggttaaa aaagaaaat gtttaacgtc tgaaaagttg agaataaggg ataattttgg | 1500 |
| gtaggtatga taaggaacaa agagtggttt tgggttttcc tagg | 1544 |

<210> SEQ ID NO 13
<211> LENGTH: 1465
<212> TYPE: DNA
<213> ORGANISM: UBQ-1
<220> FEATURE:
<223> OTHER INFORMATION:

<400> SEQUENCE: 13

| | |
|---|---|
| ggatcccttt tgtgtttcgt cttctctcac gtagaaaccc taaacaagga ggaggcgggt | 60 |
| ttatatatgt caatgtacgc gtctagggtt ttgctaatat tgggctaggt tacaggcctt | 120 |
| taccacaaaa gcttagttga taaaatattt ttatttggtt gtaattttgt aatatcccgg | 180 |
| gatatttcac aaaattgaaca tagactacag aattttagaa aacaaacttt ctctctctta | 240 |
| tctcaccttt atcttttaga gagaaaaagt tcgatttccg gttgaccgga atgtatcttt | 300 |
| gttttttttg ttttgtaaca tatttcgttt tccgatttag atcggatctc cttttccgtt | 360 |
| ttgtcggacc ttcttccggt ttatccggat ctaataatat ccatcttaga cttagctaag | 420 |
| tttggatctg tttttttggtt agctcttgtc aatcgcctca tcatcagcaa gaaggtgaaa | 480 |
| tttttgacaa ataaatctta gaatcatgta gtgtctttgg accttgggaa tgatagaaac | 540 |
| gatttgttat agctactcta tgtatcagac cctgaccaag atccaacaat ctcataggtt | 600 |
| tgtgcatat gaaaccttcg actaacgaga agtggtcttt taatgagaga gatatctaaa | 660 |
| atgttatctt aaaagcccac tcaaatctca aggcataagg tagaaatgca aatttggaaa | 720 |
| gtgggctggg ccttctgcag ttgataaaat attttttattt ggttgtaatt ttgtaatatc | 780 |
| ccgggatatt tcacaaattg aacatagact acagaatttt agaaaacaaa ctttctctct | 840 |
| cttatctcac ctttatcttt tagagagaaa aagttcgatt tccggttgac cggaatgtat | 900 |
| ctttgttttt tttgttttgt aacatatttc gttttccgat ttagatcgga tctccttttc | 960 |
| cgttttgtcg gaccttcttc cggtttatcc ggatctaata atatccatct tagacttagc | 1020 |
| taagtttgga tctgtttttt ggttagctct tgtcaatcgc ctcatcatca gcaagaaggt | 1080 |
| gaaattttg acaaataaat cttagaatca tgtagtgtct ttggaccttg ggaatgatag | 1140 |
| aaacgatttg ttatagctac tctatgtatc agaccctgac caagatccac caatctcata | 1200 |
| ggttttgtgc atatgaaacc ttcgactaac gagaagtggt cttttaatga gagagatatc | 1260 |
| taaaatgtta tcttaaaagc ccactcaaat ctcaaggcat aaggtagaaa tgcaaatttg | 1320 |
| gaaagtgggc tggccttttt gtggtaaagg cctgtaacct agcccaatat tagcaaaacc | 1380 |
| ctagacgcgt acattgacat atataaaccc gcctcctcct tgtttagggt ttctacgtga | 1440 |
| gagaagacga aacacaaaag gatcc | 1465 |

<210> SEQ ID NO 14
<211> LENGTH: 1465
<212> TYPE: DNA
<213> ORGANISM: UBQ-1
<220> FEATURE:
<223> OTHER INFORMATION:

<400> SEQUENCE: 14

| | | | | | |
|---|---|---|---|---|---|
| cctagggaaa | acacaaagca | gaagagagtg | catcttggga | atttgttcct | cctccgccca | 60 |
| aatatataca | gttacatgcg | cagatcccaa | aacgattata | acccgatcca | atgtccggaa | 120 |
| atggtgtttt | cgaatcaact | attttataaa | aataaaccaa | cattaaaaca | ttatagggcc | 180 |
| ctataaagtg | tttaacttgt | atctgatgtc | ttaaaatctt | ttgtttgaaa | gagagagaat | 240 |
| agagtggaaa | tagaaaatct | ctcttttca | agctaaaggc | caactggcct | tacatagaaa | 300 |
| caaaaaaaac | aaaacattgt | ataaagcaaa | aggctaaatc | tagcctagag | gaaaaggcaa | 360 |
| aacagcctgg | aagaaggcca | ataggccta | gattattata | ggtagaatct | gaatcgattc | 420 |
| aaacctagac | aaaaaaccaa | tcgagaacag | ttagcggagt | agtagtcgtt | cttccacttt | 480 |
| aaaaactgtt | tatttagaat | cttagtacat | cacagaaacc | tggaacccct | actatctttg | 540 |
| ctaaacaata | tcgatgagat | acatagtctg | ggactggttc | taggttgtta | gagtatccaa | 600 |
| aacacgtata | ctttggaagc | tgattgctct | tcaccagaaa | attactctct | ctatagattt | 660 |
| tacaatagaa | ttttcggtg | agtttagagt | tccgtattcc | atctttacgt | ttaaaccttt | 720 |
| cacccgaccc | ggaagacgtc | aactatttta | taaaataaaa | ccaacattaa | aacattatag | 780 |
| ggccctataa | agtgtttaac | ttgtatctga | tgtcttaaaa | tcttttgttt | gaaagagaga | 840 |
| gaatagagtg | gaaatagaaa | atctctcttt | ttcaagctaa | aggccaactg | gccttacata | 900 |
| gaaacaaaaa | aaacaaaaca | ttgtataaag | caaaggcta | aatctagcct | agaggaaaag | 960 |
| gcaaaacagc | ctggaagaag | gccaaatagg | cctagattat | tataggtaga | atctgaatcg | 1020 |
| attcaaacct | agacaaaaaa | ccaatcgaga | acagttagcg | gagtagtagt | cgttcttcca | 1080 |
| ctttaaaaac | tgtttattta | gaatcttagt | acatcacaga | aacctggaac | ccttactatc | 1140 |
| tttgctaaac | aatatcgatg | agatacatag | tctgggactg | gttctaggtt | gttagagtat | 1200 |
| ccaaaacacg | tatactttgg | aagctgattg | ctcttcacca | gaaaattact | ctctctatag | 1260 |
| attttacaat | agaattttcg | ggtgagttta | gagttccgta | ttccatcttt | acgtttaaac | 1320 |
| ctttcacccg | acccggaaaa | caccatttcc | ggacattgga | tcgggttata | atcgttttgg | 1380 |
| gatctgcgca | tgtaactgta | tatttggg | cggaggagga | acaaatccca | aagatgcact | 1440 |
| ctcttctgct | ttgtgttttc | ctagg | | | | 1465 |

<210> SEQ ID NO 15
<211> LENGTH: 1618
<212> TYPE: DNA
<213> ORGANISM: UBQ-1
<220> FEATURE:
<223> OTHER INFORMATION:

<400> SEQUENCE: 15

| | | | | | |
|---|---|---|---|---|---|
| ggatccacaa | acttacaaat | ttctctgaag | ttgtatcctc | agtacttcaa | agaaaatagc | 60 |
| ttacaccaaa | ttttttcttg | ttttcacaaa | tgccgaactt | ggttccttat | ataggaaaac | 120 |
| tcaagggcaa | aaatgacacg | gaaaaatata | aaaggataag | tagtgggga | taagattcct | 180 |
| ttgtgataag | gttactttcc | gaagcttagt | tgataaaata | ttttttattg | gttgtaattt | 240 |
| tgtaatatcc | cgggatattt | cacaaattga | acatagacta | cagaatttta | gaaaacaaac | 300 |

-continued

```
tttctctctc ttatctcacc tttatctttt agagagaaaa agttcgattt ccggttgacc      360
ggaatgtatc tttgttttt ttgttttgta acatatttcg ttttccgatt tagatcggat       420
ctccttttcc gttttgtcgg accttcttcc ggtttatccg gatctaataa tatccatctt      480
agacttagct aagtttggat ctgttttttg gttagctctt gtcaatcgcc tcatcatcag      540
caagaaggtg aaattttga caaataaatc ttagaatcat gtagtgtctt tggaccttgg       600
gaatgataga acgatttgt tatagctact ctatgtatca gaccctgacc aagatccaac      660
aatctcatag gttttgtgca tatgaaacct tcgactaacg agaagtggtc ttttaatgag     720
agagatatct aaaatgttat cttaaaagcc cactcaaatc tcaaggcata aggtagaaat     780
gcaaatttgg aaagtgggct gggccttctg cagttgataa atattttta tttggttgta      840 attttgtaat atcccgggat atttcacaaa ttgaacatag actacagaat tttagaaaac     900
aaactttctc tctcttatct cacctttatc ttttagagag aaaaagttcg atttccggtt     960
gaccggaatg tatctttgtt ttttttgttt tgtaacatat ttcgttttcc gatttagatc    1020
ggatctcctt ttccgttttg tcggaccttc ttccggttta tccggatcta ataatatcca    1080
tcttagactt agctaagttt ggatctgttt tttggttagc tcttgtcaat cgcctcatca    1140
tcagcaagaa ggtgaaattt ttgacaaata atcttagaa tcatgtagtg tctttggacc     1200
ttgggaatga tagaaacgat tgttatagc tactctatgt atcagaccct gaccaagatc     1260
caacaatctc ataggttttg tgcatatgaa accttcgact aacgagaagt ggtcttttaa   1320
tgagagagat atctaaaatg ttatcttaaa agcccactca atctcaagg cataaggtag    1380 aaatgcaaat ttggaaagtg ggctgggcct tggtacccgg aaagtaaccct tatcacaaag   1440 gaatcttatc ccccactact tatccttta tatttttccg tgtcattttt gcccttgagt    1500
tttcctatat aaggaaggaa gttcggcatt tgtgaaaaca agaaaaaatt tggtgtaagc   1560
tattttcttt gaagtactga ggatacaact tcagagaaat ttgtaagttt gtggatcc      1618
```

<210> SEQ ID NO 16
<211> LENGTH: 1618
<212> TYPE: DNA
<213> ORGANISM: UBQ-1
<220> FEATURE:
<223> OTHER INFORMATION:

<400> SEQUENCE: 16

```
cctaggtgtt tgaatgttta aagagacttc aacataggag tcatgaagtt tcttttatcg      60
aatgtggttt aaaaaagaac aaaagtgttt acggcttgaa ccaaggaata tatccttttg     120
agttcccgtt tttactgtgc ctttttatat tttcctattc atcacccct attctaagga     180 aacactattc caatgaaagg cttcgaatca actattttat aaaaataaac caacattaaa    240
acattatagg gccctataaa gtgtttaact tgtatctgat gtcttaaaag cttttgtttg    300
aaagagagag aatagagtgg aaatagaaaa tctctctttt tcaagctaaa ggccaactgg    360
ccttacatag aaacaaaaaa aacaaaacat tgtataaagc aaaaggctaa atctagccta    420
gaggaaaagg caaaacagcc tggaagaagg ccaaataggc ctagattatt ataggtagaa    480
tctgaatcga ttcaaaccta gacaaaaaac caatcgagaa cagttagcgg agtagtagtc    540
gttcttccac tttaaaaact gtttatttag aatcttagta catcacagaa acctggaacc    600
cttactatct ttgctaaaca atatcgatga gatacatagt ctgggactgg ttctaggttg    660
ttagagtatc caaaacacgt atactttgga agctgattgc tcttcaccag aaaattactc    720
tctctataga ttttacaata gaattttcgg gtgagtttag agttccgtat tccatcttta    780
```

```
cgtttaaacc tttcacccga cccggaagac gtcaactatt ttataaaaat aaaccaacat      840
taaaacatta tagggcccta taaagtgttt aacttgtatc tgatgtctta aaatcttttg      900
tttgaaagag agagaataga gtggaaatag aaaatctctc ttttcaagc taaaggccaa       960 ctggccttac atagaaacaa aaaaaacaaa acattgtata aagcaaaagg ctaaatctag     1020
cctagaggaa aaggcaaaac agcctggaag aaggccaaat aggcctagat tattataggt     1080
agaatctgaa tcgattcaaa cctagacaaa aaaccaatcg agaacagtta gcggagtagt    1140
agtcgttctt ccactttaaa aactgtttat ttagaatctt agtacatcac agaaacctgg    1200
aacccttact atctttgcta acaatatcg atgagataca tagtctggga ctggttctag     1260
gttgttagag tatccaaaac acgtatactt tggaagctga ttgctcttca ccagaaaatt    1320
actctctcta tagattttac aatagaattt tcgggtgagt ttagagttcc gtattccatc    1380
tttacgttta aacctttcac ccgacccgga accatgggcc tttcattgga atagtgtttc    1440
cttagaatag ggggtgatga ataggaaaat ataaaaggc acagtaaaaa cgggaactca    1500
aaaggatata ttccttggtt caagccgtaa acacttttgt tctttttaa accacattcg     1560 ataaaagaaa cttcatgact cctatgttga agtctcttta acattcaaa cacctagg       1618

<210> SEQ ID NO 17
<211> LENGTH: 1524
<212> TYPE: DNA
<213> ORGANISM: CaMV 35S
<220> FEATURE:
<223> OTHER INFORMATION:

<400> SEQUENCE: 17
ggatccagcg tgtcctctcc aaatgaaatg aacttcctta tatagaggaa gggtcttgcg       60
aaggatagtg ggattgtgcg tcatcccta cgtcagtgga gatactgcag aagcttcaga     120
ctcattaact aaaagaaga tatagactca ttaacttaaa agaagatata gattccaaca       180
caagttcaaa attcataaac gtcaatcttg gctaaatttc tgaacatcaa tgcattcctt      240
taaaatatag ataataagtt aggatgttgt cactttctta aagcatattc cgactgagtc      300
tggtagaatc tcataaactt taggccttat ctcttcaatt aggcaattac ttacctccgc     360
tctactttaa gaaaattcaa tggagtacac cattattaag ttcatataaa aataaaatta     420
tattaattct gtctcttgtt ggttcgctct atcttttct gttttcctgc ttcaaccata       480
acatatacaa gaactacatt ttccaagcta gatatatcta acatgactga ctttgtaaat      540
ttcttttgcc aagttaaaga aaaaaatga tgttatccaa ataataaaga gaaagagccc       600
taatgaaaaa aatgatttac tattagagtt gttcagctaa tcacatcaat tatggttttc       660
atcaagtatg actaatggcg gctcttatct cacgtgatgt gacattgaaa ttctttgact      720
ttaacactaa tgtcatatgc tttcaaatta ataatccgat aaagctgcag actcattaac    780
ttaaaagaag atatagactc attaacttaa aagaagatat agattccaac acaagttcaa    840
aattcataaa cgtcaatctt ggctaaattt ctgaacatca atgcattcct ttaaaatata     900
gataataagt taggatgttg tcactttctt aaagcatatt ccgactgagt ctggtagaat    960
ctcataaact ttaggcctta tctcttcaat taggcaatta cttacctccg ctctactttta   1020 agaaaattca atggagtaca ccattattaa gttcatataa aaataaaatt atattaattc    1080
tgtctcttgt tggttcgctc tatcttttct gttttcctg cttcaaccat aacatataca    1140
```

```
agaactacat tttccaagct agatatatct aacatgactg actttgtaaa tttcttttgc    1200
caagttaaag aaaaaaaatg atgttatcca ataataaag agaaagagcc ctaatgaaaa     1260
aaatgattta ctattagagt tgttcagcta atcacatcaa ttatggtttt catcaagtat    1320
gactaatggc ggctcttatc tcacgtgatg tgacattgaa attctttgac tttaacacta    1380
atgtcatatg ctttcaaatt aataatccga taaaggtacc tatctccact gacgtaaggg    1440
atgacgcaca atcccactat ccttcgcaag acccttcctc tatataagga agttcatttc    1500
atttggagag gacacgctgg atcc                                           1524
```

<210> SEQ ID NO 18
<211> LENGTH: 1524
<212> TYPE: DNA
<213> ORGANISM: CaMV 35S
<220> FEATURE:
<223> OTHER INFORMATION:

<400> SEQUENCE: 18

```
cctaggtcgc acaggagagg tttactttac ttgaaggaat atatctcctt cccagaacgc    60
ttcctatcac cctaacacgc agtagggaat gcagtcacct ctatgacgtc ttcgaagtct    120
gagtaattga atttcttct atatctgagt aattgaattt cttctatat ctaaggttgt     180 gttcaagttt taagtatttg cagttagaac cgatttaaag acttgtagtt acgtaaggaa    240
attttatatc tattattcaa tcctacaaca gtgaaagaat ttcgtataag gctgactcag    300
accatcttag agtatttgaa atccggaata gagaagttaa tccgttaatg aatggaggcg    360
agatgaaatt cttttaagtt acctcatgtg gtaataattc aagtatattt ttatttttaat   420 ataattaaga cagagaacaa ccaagcgaga tagaaaaaga caaaaggacg aagttggtat    480
tgtatatgtt cttgatgtaa aaggttcgat ctatatagat tgtactgact gaaacattta    540
aagaaaagcc ttcaatttct tttttttact acaataggtt tattatttct ctttctcggg    600 attactttt ttactaaaatg ataatctcaa caagtcgatt agtgtagtta ataccaaaag     660
tagttcatac tgattaccgc cgagaataga gtgcactaca ctgtaacttt aagaaactga    720
aattgtgatt acagtatacg aaagtttaat tattaggcta tttcgacgtc tgagtaattg    780 aatttcttc tatatctgag taattgaatt ttccttctata tctaaggttg tgttcaagtt    840
ttaagtattt gcagttagaa ccgatttaaa gacttgtagt tacgtaagga attttatat    900 ctattattca atcctacaac agtgaaagaa ttcgtataa ggctgactca gaccatctta    960
gagtatttga atccggaat agagaagtta atccgttaat gaatggaggc gagatgaaat    1020
tcttttaagt tacctcatgt ggtaataatt caagtatatt ttatttta tataattaag    1080 acagagaaca accaagcgag atagaaaaag acaaaaggac gaagttggta ttgtatatgt   1140
tcttgatgta aaaggttcga tctatataga ttgtactgac tgaaacattt aaagaaaacg    1200
gttcaatttc tttttttac tacaataggt ttattatttc tctttctcgg gattactttt     1260
tttactaaat gataatctca acaagtcgat tagtgtagtt aataccaaaa gtagttcata    1320
ctgattaccg ccgagaatag agtgcactac actgtaactt taagaaactg aaattgtgat    1380
tacagtatac gaaagtttaa ttattaggct atttccatgg atagaggtga ctgcattccc    1440
tactgcgtgt tagggtgata ggaagcgttc tgggaaggag atatattcct tcaagtaaag    1500
taaacctctc ctgtgcgacc tagg                                           1524
```